United States Patent
Zhou et al.

(10) Patent No.: US 12,275,035 B2
(45) Date of Patent: Apr. 15, 2025

(54) SWAB FLOCKING DEVICE, AND FLOCK BLOWING AND FLOCKING PROCESS FOR SWAB

(71) Applicant: Bioteke Corporation (Wuxi) Co., Ltd., Wuxi (CN)

(72) Inventors: Zhitu Zhou, Wuxi (CN); Junli Ji, Wuxi (CN)

(73) Assignee: Bioteke Corporation (Wuxi) Co., Ltd., Wuxi (CN)

( * ) Notice: Subject to any disclaimer, the term of this patent is extended or adjusted under 35 U.S.C. 154(b) by 282 days.

(21) Appl. No.: 18/048,355

(22) Filed: Oct. 20, 2022

(65) Prior Publication Data
US 2023/0234093 A1  Jul. 27, 2023

(30) Foreign Application Priority Data
Jan. 22, 2022 (CN) .......................... 202210075127.4

(51) Int. Cl.
*B05C 19/00* (2006.01)
*B05C 13/02* (2006.01)
*B05D 1/14* (2006.01)
*B05D 3/14* (2006.01)

(52) U.S. Cl.
CPC ............ *B05C 19/001* (2013.01); *B05C 13/02* (2013.01); *B05D 1/14* (2013.01); *B05D 3/142* (2013.01)

(58) Field of Classification Search
CPC .................................................... A61F 13/385
See application file for complete search history.

(56) References Cited

U.S. PATENT DOCUMENTS

| | | | |
|---|---|---|---|
| 2004/0213942 A1* | 10/2004 | Sano | C09J 7/38 428/40.1 |
| 2008/0034609 A1* | 2/2008 | Wolf | D06F 73/02 34/216 |
| 2011/0282243 A1* | 11/2011 | Nakatani | A45D 34/04 606/162 |

FOREIGN PATENT DOCUMENTS

| | | | |
|---|---|---|---|
| CN | 1570003 A | 1/2005 | |
| CN | 1672808 A | 9/2005 | |
| CN | 202087497 U | 12/2011 | |
| CN | 110449325 A | 11/2019 | |
| CN | 210935749 U | 7/2020 | |
| CN | 111822282 A | * 10/2020 | ............ B05C 13/02 |
| CN | 112221887 A | 1/2021 | |
| CN | 213670264 U | 7/2021 | |
| CN | 214637944 U | * 11/2021 | |

(Continued)

OTHER PUBLICATIONS

International Search Report dated Sep. 28, 2022, for corresponding PCT Application No. PCT/CN2022/075508.

(Continued)

*Primary Examiner* — Michael P. Rodriguez
(74) *Attorney, Agent, or Firm* — Kinney & Lange, P.A.

(57) ABSTRACT

Disclosed are a swab flocking device and a flock blowing and flocking process for a swab. A conveying drag chain transversely penetrates through a flocking box, several swab hangers are arranged on the conveying drag chain at intervals, and the conveying drag chain is connected to a first motor. Several blowers are arranged on an outer side of the conveying drag chain in the flocking box. During flocking, a swab stick is hung on the swab hanger and then is conveyed forwards by the conveying drag chain, and several blowers are configured to blow flocks onto an end head of the swab stick.

14 Claims, 31 Drawing Sheets

(56) References Cited

FOREIGN PATENT DOCUMENTS

| | | |
|---|---|---|
| CN | 113814140 A | 12/2021 |
| JP | 2002153802 A | 5/2002 |
| WO | 2019137069 A1 | 7/2019 |
| WO | 2021217025 A1 | 10/2021 |

OTHER PUBLICATIONS

English Translation of first Chinese Office Action dated Oct. 11, 2024, for corresponding Chinese Patent Application No. 202210075127.4, 7 pgs.

* cited by examiner

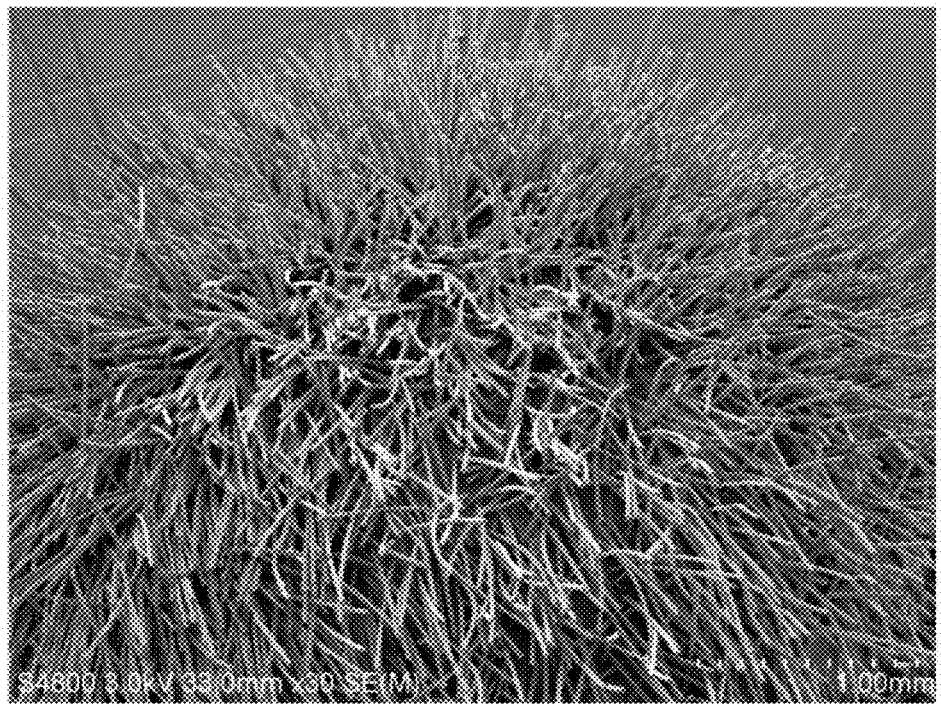
FIG. 16A1
FIG. 16A2

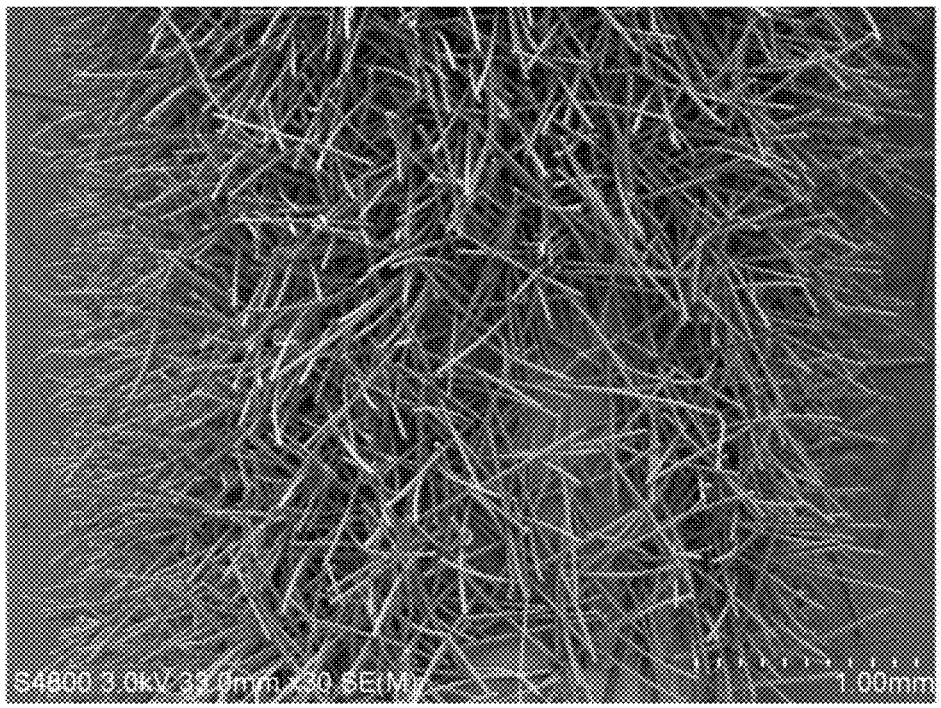
FIG. 16A3
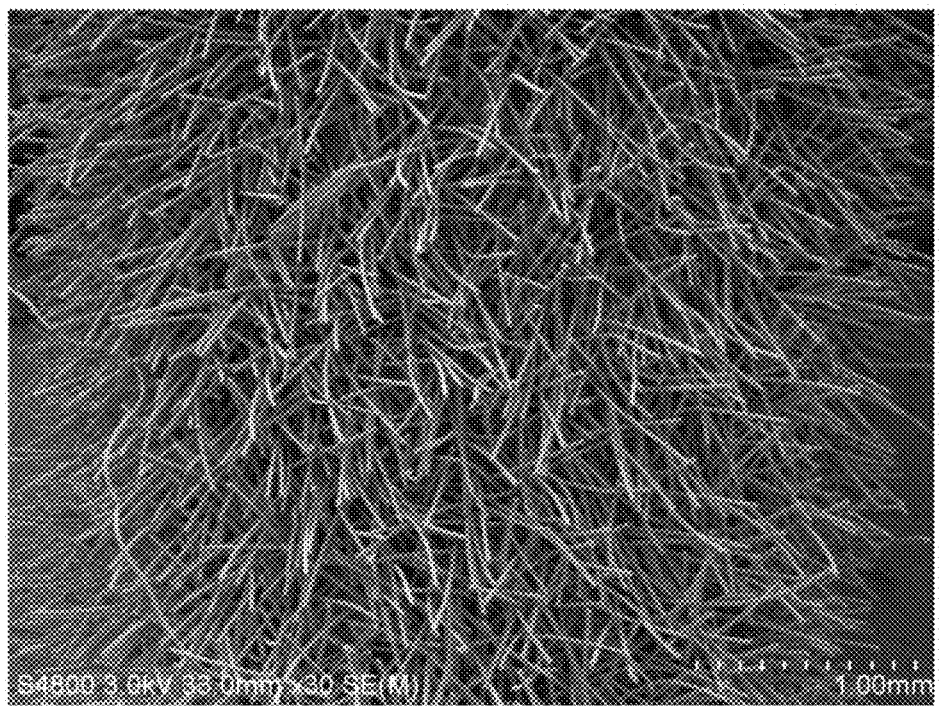
FIG. 16A4

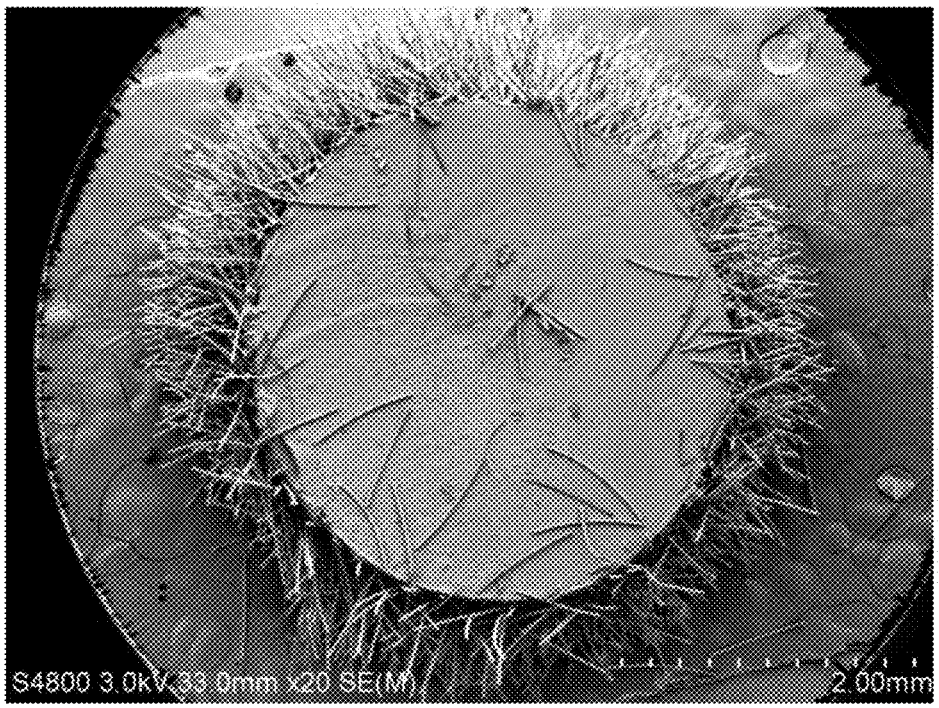
FIG. 16B1
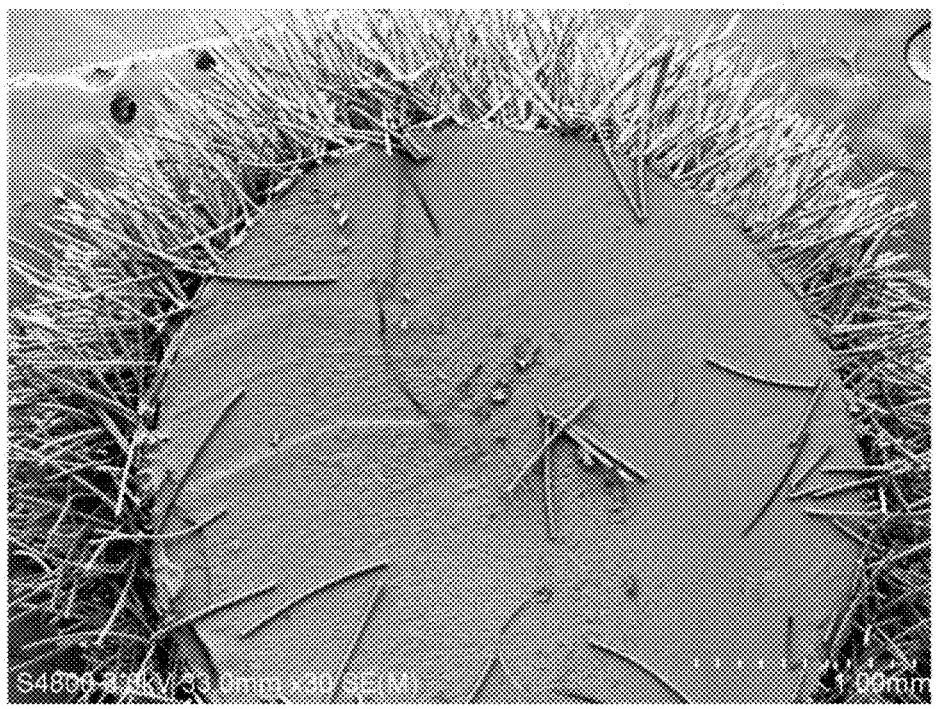
FIG. 16B2

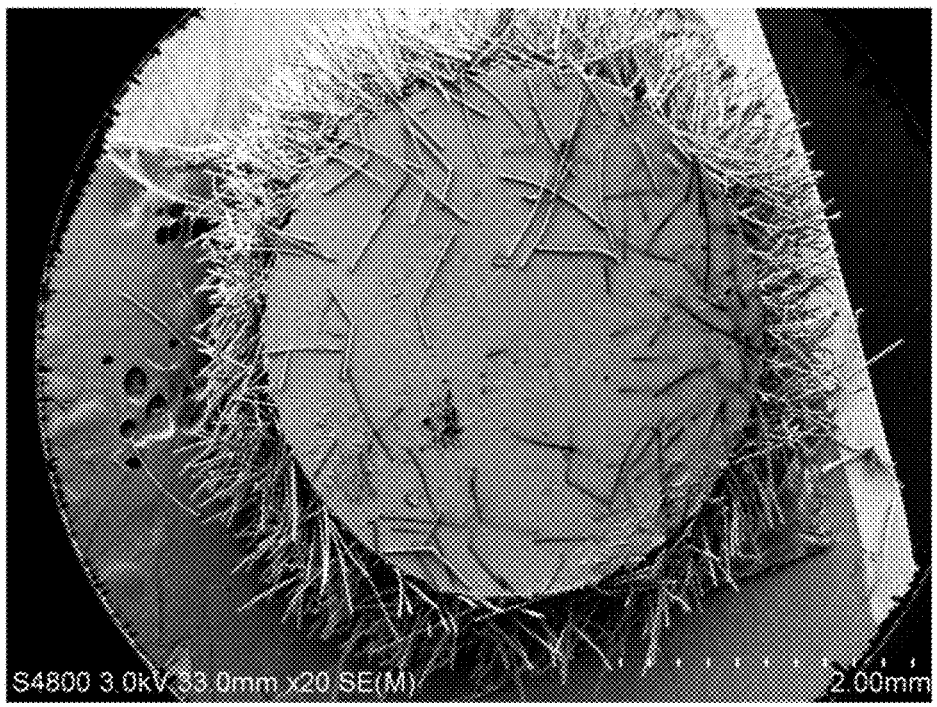
FIG. 16B3
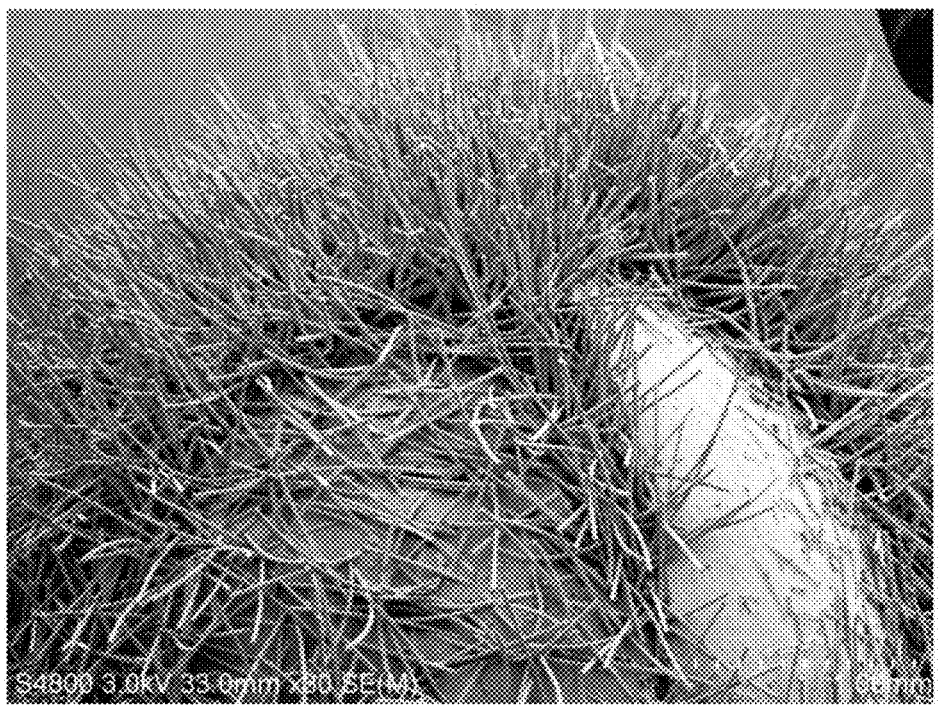
FIG. 17A1

FIG. 17A2
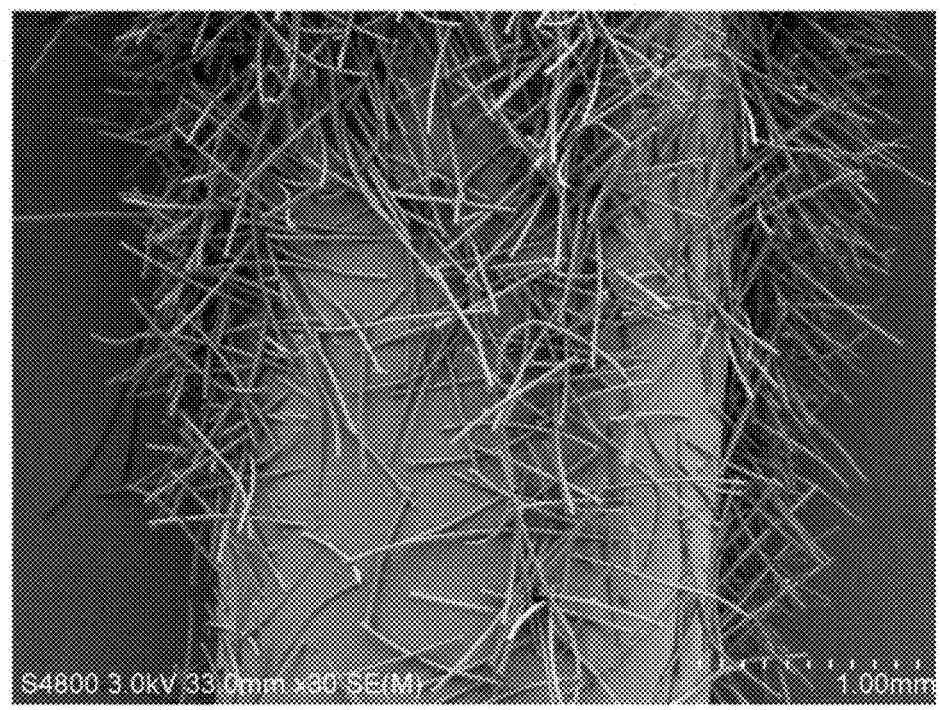
FIG. 17A3

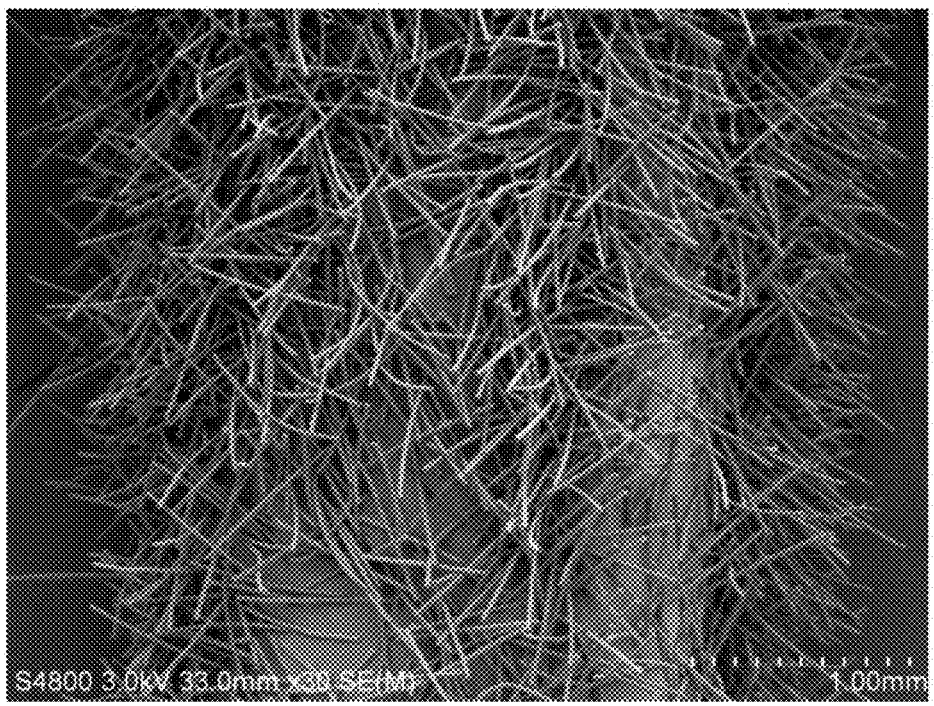
FIG. 17A4
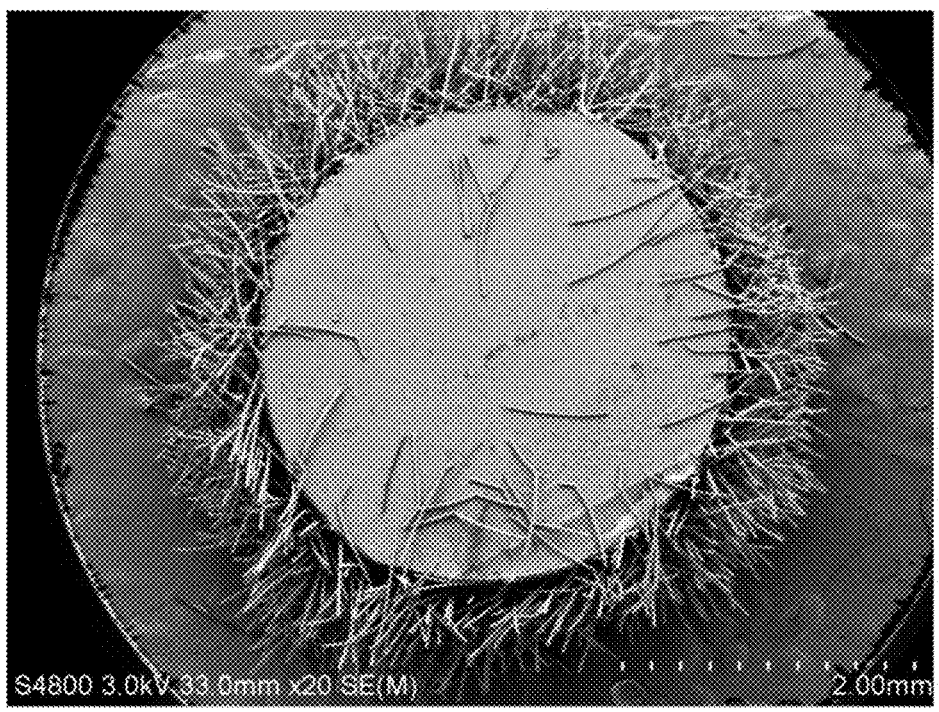
FIG. 17B1

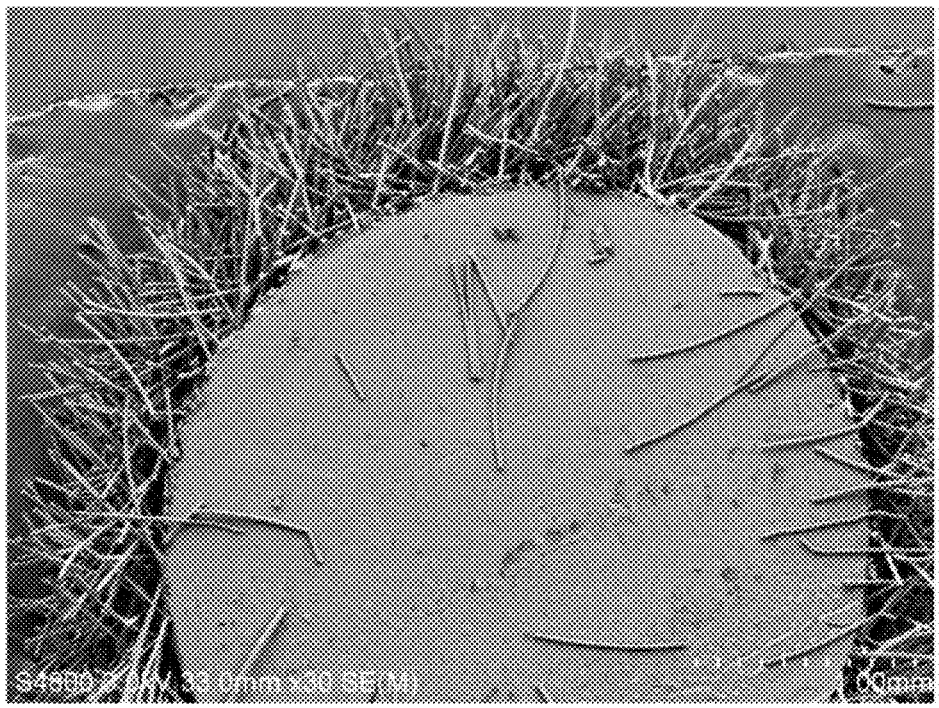
FIG. 17B2
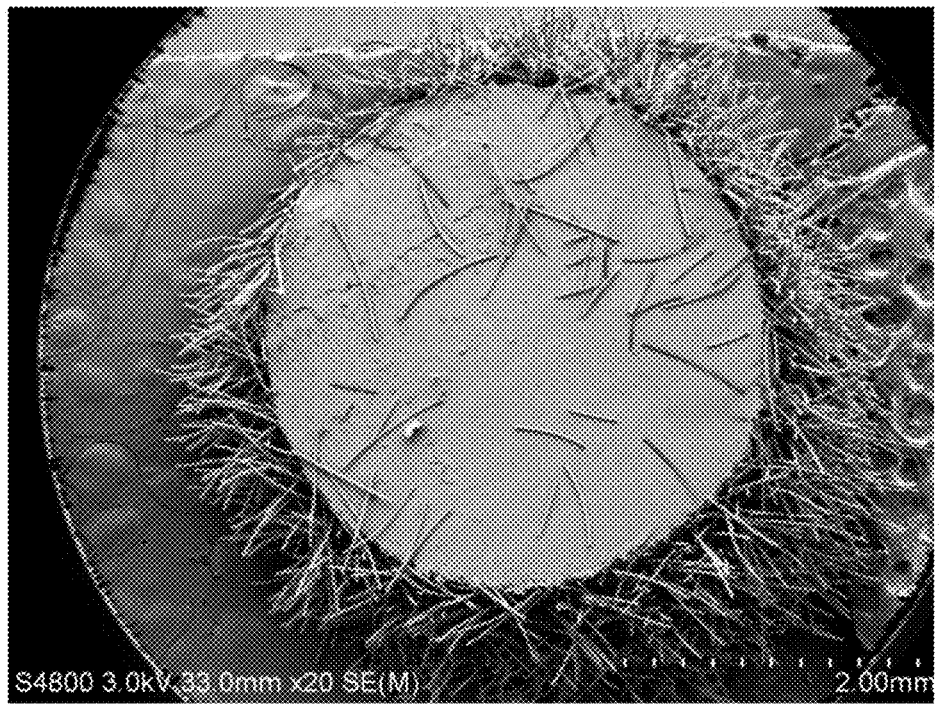
FIG. 17B3

SWAB FLOCKING DEVICE, AND FLOCK BLOWING AND FLOCKING PROCESS FOR SWAB

CROSS-REFERENCE TO RELATED APPLICATION(S)

This application claims the benefit and priority of Chinese Patent Application No. 202210075127.4 filed on Jan. 22, 2022, the disclosure of which is incorporated by reference herein in its entirety as part of the present application.

TECHNICAL FIELD

The present disclosure relates to the technical field of swab flocking, and in particular relates to a swab flocking device for flocking using a flock blowing mode, and a flock blowing and flocking process for a swab.

BACKGROUND

In the medical field, a method for performing sampling and transferring samples to a related test center by using medical sampling swab has been widely used. A common medical sampling swab includes a swab stick and a swab head, the swab stick is a handheld part, and the swab head is a part which is fixed at one end of the swab stick and capable of effectively adsorbing a biological sample. The swab head is configured for medicine application, or for wiping over a certain area. The swabs are typically used as a medical examination tool for collecting microorganisms, exfoliated cells or secretions.

In the prior art, the swab is usually produced by utilizing an electrostatic flocking principle. A swab that needs to be flocked is placed in a high-voltage electrostatic field, the flocks are attracted by a different-potential object to be flocked and vertically accelerated to fly to a surface of the object that needs to be flocked. As the object to be flocked is coated with an adhesive, the flocks are vertically adhered to the object to be flocked. Electrostatic flocking is a production process that takes advantage of the natural characteristics of electric charges. However, the electrostatic flocking process method requires a high-voltage electrostatic generator to be provided in the flocking device, and the high-voltage electric field required for flocking is generated by the high-voltage electrostatic generator, which requires a large amount of electrical energy, more power consumption and higher energy consumption. Moreover, electrostatic flocking is prone to electrostatic effects, generating electrostatic discharge and electrostatic sparks, leading to safety risks, and meanwhile, the flocking effect is affected, and further the quality of swabs is affected.

SUMMARY

For the shortcomings in the production of the swab using the existing electrostatic flocking process, a swab flocking device with a reasonable structure and a flock blowing and flocking process for a swab are provided. The swab is flocked in a flock blowing mode, such that the requirement for electric energy is reduced, energy consumption is decreased, and the electrostatic effect is avoided.

The technical solution employed by the present disclosure is as follows:

A swab flocking device, wherein a conveying drag chain transversely penetrates through a flocking box, several swab hangers are arranged on the conveying drag chain at intervals, and the conveying drag chain is connected to a first motor; several blowers are arranged at an outer side of the conveying drag chain in the flocking box; during flocking, a swab stick is hung on each of the swab hangers and is conveyed forwards by the conveying drag chain, and the several blowers are configured to blow flocks onto an end head of the swab stick.

Further improvements of the technical solution are also provided.

The blowers include lateral blowers which are respectively arranged around a swab hanger at a central part of the flocking box, and each lateral blower is configured to laterally blow air towards the swab hanger at the central part of the flocking box.

The blowers include a vertical blower arranged at a center of a bottom of the flocking box and directly facing the conveying drag chain, and the vertical blower is configured to vertically blow air to the swab hanger at the central part of the flocking box.

Several shaft rods are fixed to the conveying drag chain at a uniform interval, and rotation gears are rotatably connected to the shaft rods; a fixing frame is arranged on an inner surface of the flocking box, several fixed gears are arranged on a frame rod of the fixing frame at intervals, and a height position of each fixed gear matches with a height position of a respective rotation gear; and when the rotation gears follow the conveying drag chain to advance to positions of the fixed gears, the rotation gears are meshed with the fixed gears.

A hanging ring is arranged at a bottom surface of each rotation gear; a hook is arranged on a top surface of each of the swab hangers, and each of the swab hangers is hung on the hanging ring of each the rotation gear by the hook respectively.

A filter is arranged above the conveying drag chain in the flocking box, the filter is at an upper side thereof provided with a movable sweeping plate; the sweeping plate is connected to a second motor by a belt; sliders are fixedly arranged on an outer surface of the sweeping plate, slide rails are correspondingly arranged on an inner surface of the flocking box, and the sliders (13) are slidingly arranged on the slide rails.

Several hanging plates are arranged on each swab hanger at a uniform interval, two ends of each hanging plate are fixed to a bottom surface of said each swab hanger by fixing grooves respectively; several swab sticks are hung on each hanging plate; and grids are arranged on a circumferential surface of the flocking box in correspondence to the lateral blowers.

A flock blowing and flocking process for a swab, which employs any of the swab flocking devices above described for flocking, includes the following steps:

hanging a swab stick on a swab hanger, and conveying the swab hanger into a flocking box by a conveying drag chain; and blowing flocks by blowers to an end head of the swab stick in the flocking box.

Further improvements of the technical solution are provided.

The process includes performing plasma treatment, gluing and spin coating treatment on the end head of the swab stick in sequence, prior to conveying the swab stick into the flocking box; and drying the swab stick, after the flock blowing to the swab stick is completed.

A flock density of flocking is in a range between 3.8 to 6.0 Dtex, and a flock length is in a range between 0.4 to 0.6 mm.

The present disclosure has the advantageous effects as follows:

According to the present disclosure, the swab stick is flocked in a flock blowing mode, so that the flocks are uniformly adhered to the surface of the swab stick, and the flocking effect is good. In the flocking process, only blowers are required for supplying wind power. Compared with an electrostatic flocking mode, the demand for electric energy is greatly reduced, the power consumption is decreased, the energy consumption is lowered, and the electrostatic effect in the flocking process is also avoided, therefore ensuring the flocking effect and in turn the swab quality.

According to the present disclosure, the lateral blowers, which are respectively arranged around a swab hanger at a central part of the flocking box, are configured to blow air to four sides of the swab stick, such that the flocks can be blown to the swab stick on the swab hanger from four sides, it is more beneficial that the flocks are uniformly adhered to each part of the swab stick, making the flocking more uniform and the flocking effect better. The vertical blower at the bottom is configured to blow air towards the bottom of the swab stick, which is favorable that the flocks are blown towards the bottom surface of the end head of the swab stick, and the flocks are uniformly adhered and distributed to the bottom surface of the swab stick, making the flocking more uniform and the flocking effect better.

According to the present disclosure, the swab hanger is hung on the rotation gear, the rotation gear is meshed with the fixed gear in the process of moving forward, and the swab hanger can rotate along with the rotation gear, such that each surface of the swab stick can be blown by the lateral blowers, and the flocks can fall and adhere to the surface of the swab stick more uniformly, making the flocking effect better.

According to the present disclosure, the filter can be configured to filter the flocks, and the back-forth movement of the sweeping plate can generate friction on the flocks on the filter, which is more convenient for the flocks to pass through the filter to fall into a lower cavity of the flocking box.

BRIEF DESCRIPTION OF THE DRAWINGS

FIG. 16A1 to FIG. 16A4, and FIG. 16B1 to FIG. 16B3 are enlarged views of a nasal swab after spin coating treatment under the electron microscope.

FIG. 17A1 to FIG. 17A4, and FIG. 17B1 to FIG. 17B3 are enlarged views of a nasal swab without spin coating treatment under the electron microscope.

NUMERAL SIGNS 1 flocking box; 2 filter; 3 sweeping plate; 4 conveying drag chain; 41 chain wheel; 42 shaft rod; 43 rotation gear; 44 hanging ring; 5 swab hanger; 51 hook; 52 hanging plate; 53 fixing groove; 6 fixing frame; 61 frame rod; 62 fixed gear; 7 lateral blower; 8 vertical blower; 9 first motor; 10 second motor; 11 belt; 12 slide rail; 13 slider; 14 perforation; 15 grid; 20 swab stick.

DETAILED DESCRIPTION OF THE EMBODIMENTS

Embodiments of the present disclosure are described below with reference to the accompanying drawings.

Figure 1:
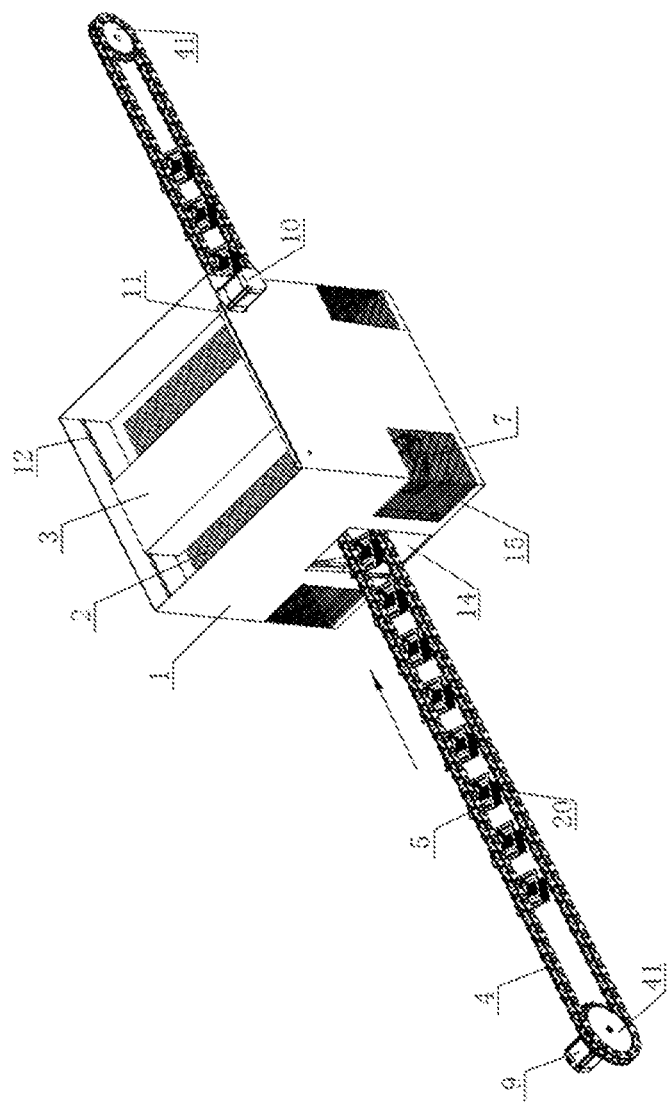
FIG. 1 is a perspective diagram of the present disclosure, in which an arrow shows an advancing direction of the conveying drag chain.
Figure 2:
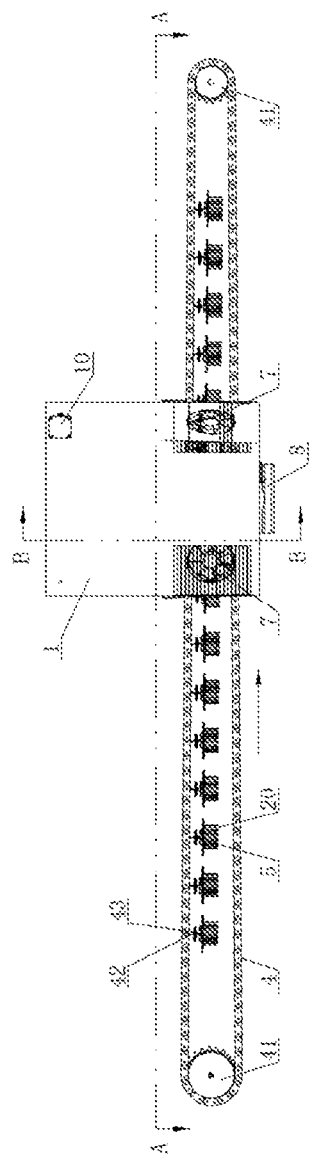
FIG. 2 is a front view of FIG. 1, in which an arrow shows the advancing direction of the conveying drag chain.

As shown in FIG. 1 and FIG. 2, perforations 14 are correspondingly formed in middle parts of a left side surface and a right side surface of a lower part of a flocking box 1, respectively. A conveying drag chain 4 transversely penetrates through the perforations 14 of the flocking box 1, that is, the conveying drag chain 4 transversely penetrates through a center of the lower part of the flocking box 1. Several swab hangers 5 are arranged on the conveying drag chain 4 at intervals. Chain wheels 41 are connected to both ends of the conveying drag chain 4. The chain wheel 41 at one end is connected to a first motor 9, and the first motor 9 is configured to drive the conveying drag chain 4 to move through the chain wheel 41, thus driving the swab hangers 5 to move forward.

Figure 4:
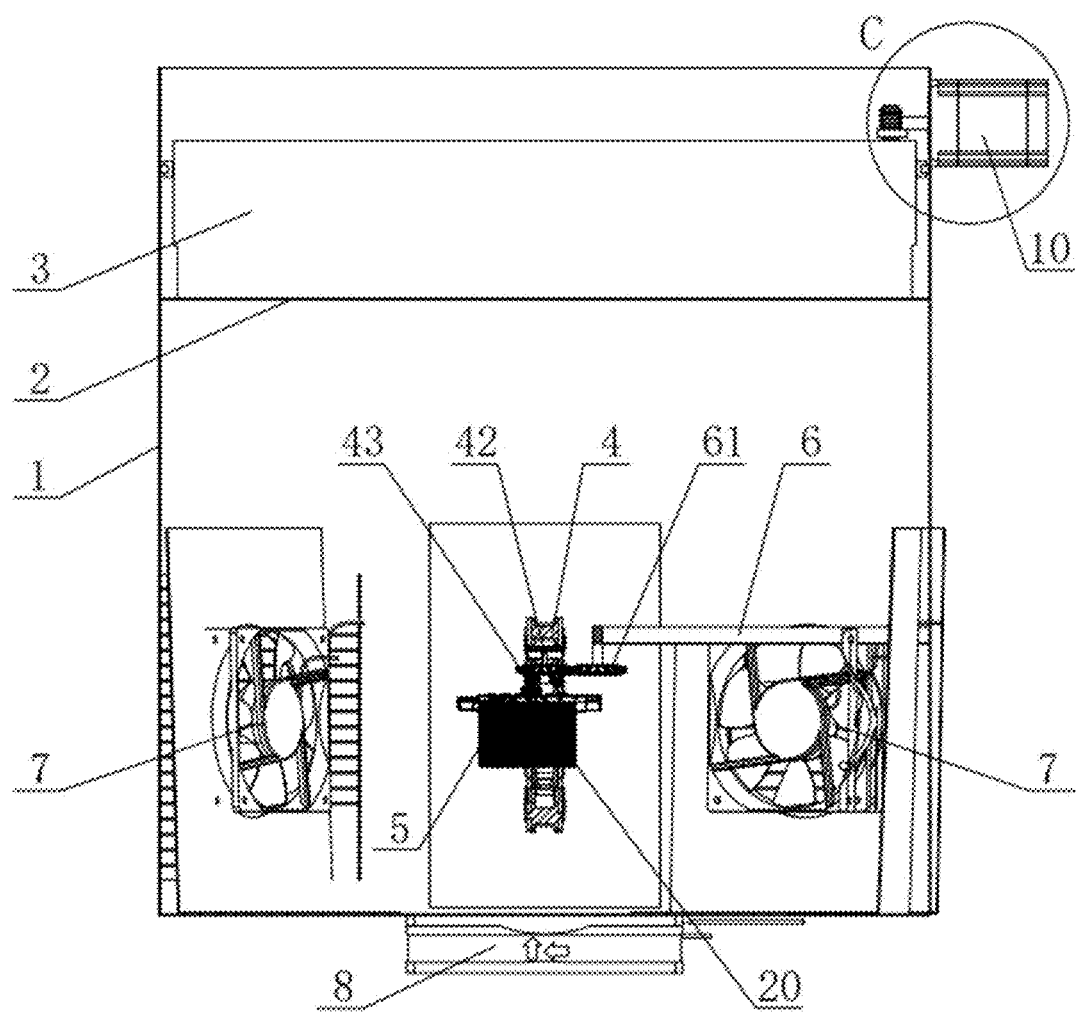
FIG. 4 is a sectional view taken along a section B-B in FIG. 2.
Figure 5:
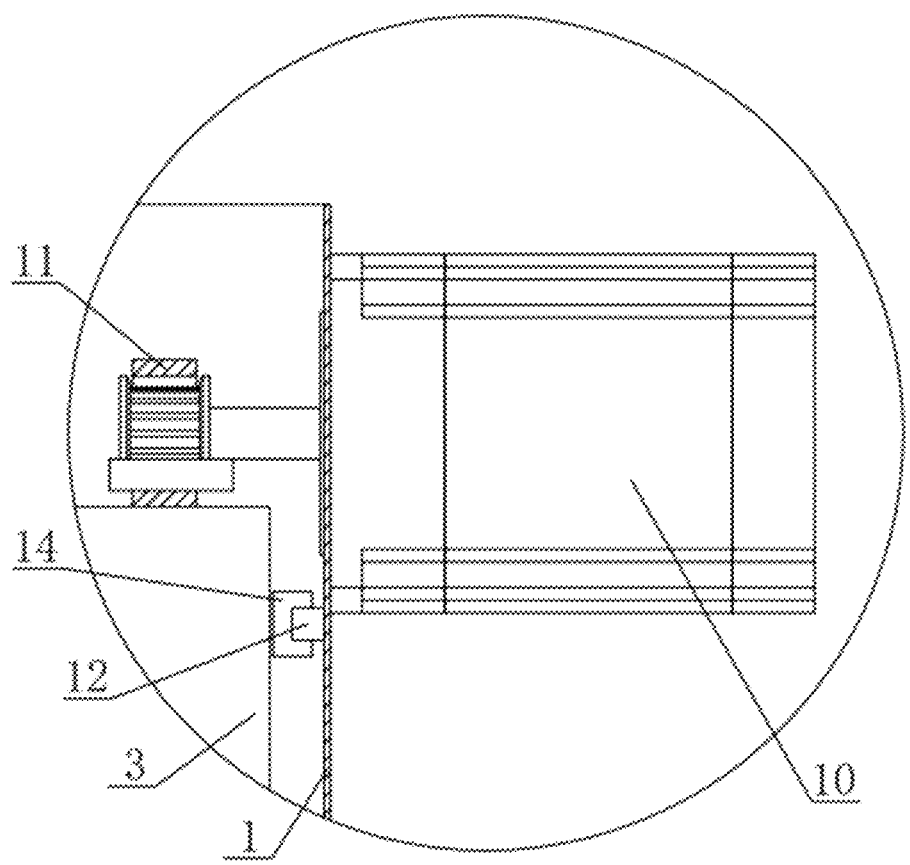
FIG. 5 is an enlarged view of a circle part C in FIG. 4.

As shown in FIG. 1 and FIG. 4, a filter 2 is arranged above the conveying drag chain 4 in the flocking box 1, and a movable sweeping plate 3 is arranged at an upper side of the filter 2. As shown in FIG. 4 and FIG. 5, sliders 13 are fixedly arranged on outer surfaces of a front side and a rear side of the sweeping plate 3, and slide rails 12 are correspondingly arranged at inner surfaces of a front side and a rear side of the flocking box 1, and the sliders 13 are slidingly arranged on the slide rails 12. The sweeping plate 3 is connected to a second motor 10 by a belt 11, the second motor 10 can drive the sweeping plate 3 to move back and forth on the filter 2 along the slide rails 12 via the belt 11. The filter 2 can be configured to filter the flocks, and the back-forth movement of the sweeping plate 3 can generate friction on the flocks on the filter 2, which is more beneficial for the flocks to pass through the filter 2 to fall into a lower cavity of the flocking box 1.

Figure 3:
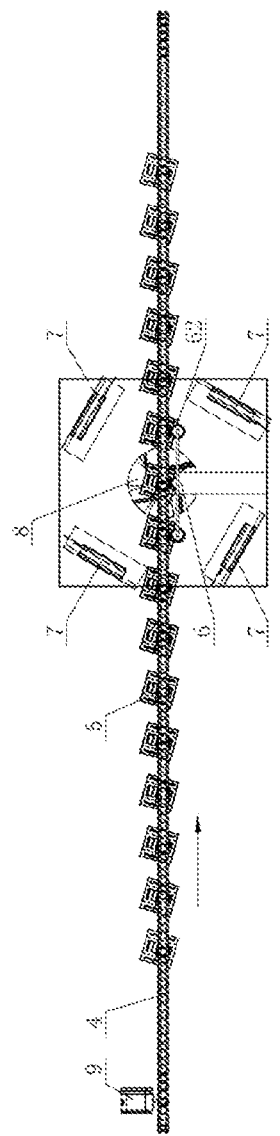
FIG. 3 is a sectional view taken along a section A-A in FIG. 2, in which an arrow shows the advancing direction of the conveying drag chain.
Figure 6:
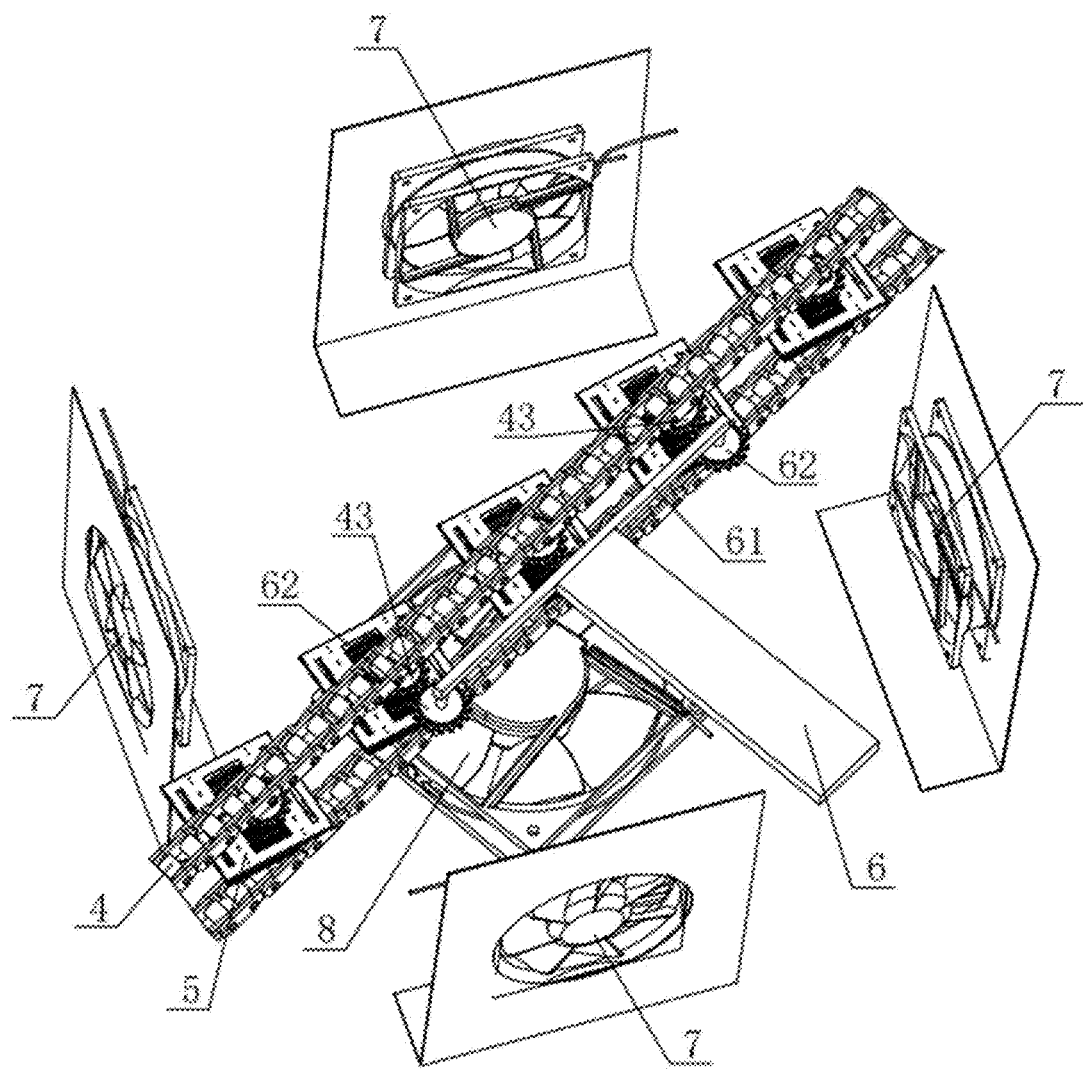
FIG. 6 is a schematic diagram of a partial structure of an interior of a flocking box in accordance with the present disclosure.

As shown in FIG. 2 to FIG. 4, several lateral blowers 7 are respectively arranged around a swab hanger 5 at a central part of the flocking box 1. As shown in FIG. 2 and FIG. 6, in the present embodiment, four lateral blowers 7 are respectively arranged on outside the conveying drag chain 4, and are respectively arranged around the swab hanger 5 at the central part of the flocking box 1, and each lateral blower 7 is configured to laterally blow air towards the swab hanger 5 at the center part of the flocking box 1. The lateral blowers 7 arranged around the swab hanger 5 are configured to blow air towards four sides of the central swab hanger 5, such that the flocks are blown to the swab stick 20 on the swab hanger 5 from four sides, which is more advantageous for the flocks to be evenly adhered and distributed to all parts of the swab stick 20, making the flocking more uniform and the flocking effect better. A vertical blower 8 is arranged at a center of a bottom of the flocking box 1 to directly face the conveying drag chain 4. The vertical blower 8 is configured to vertically blow air to the swab hanger at the center part of the flocking box 1. The vertical blowers 8 at the bottom is configured to blow air towards a bottom of the swab stick 20 at the center swab hanger 5, which is advantageous for the flocks to be blown to a bottom surface of an end head of the swab stick 20, and for the flocks to be evenly adhered and distributed to the bottom surface of the swab stick 20, making the flocking more uniform and the flocking effect better. As shown in FIG. 1, grids 15 are arranged on a circumferential surface of the flocking box 1 to correspond to the lateral blowers 7 for ventilation.

Figure 8:
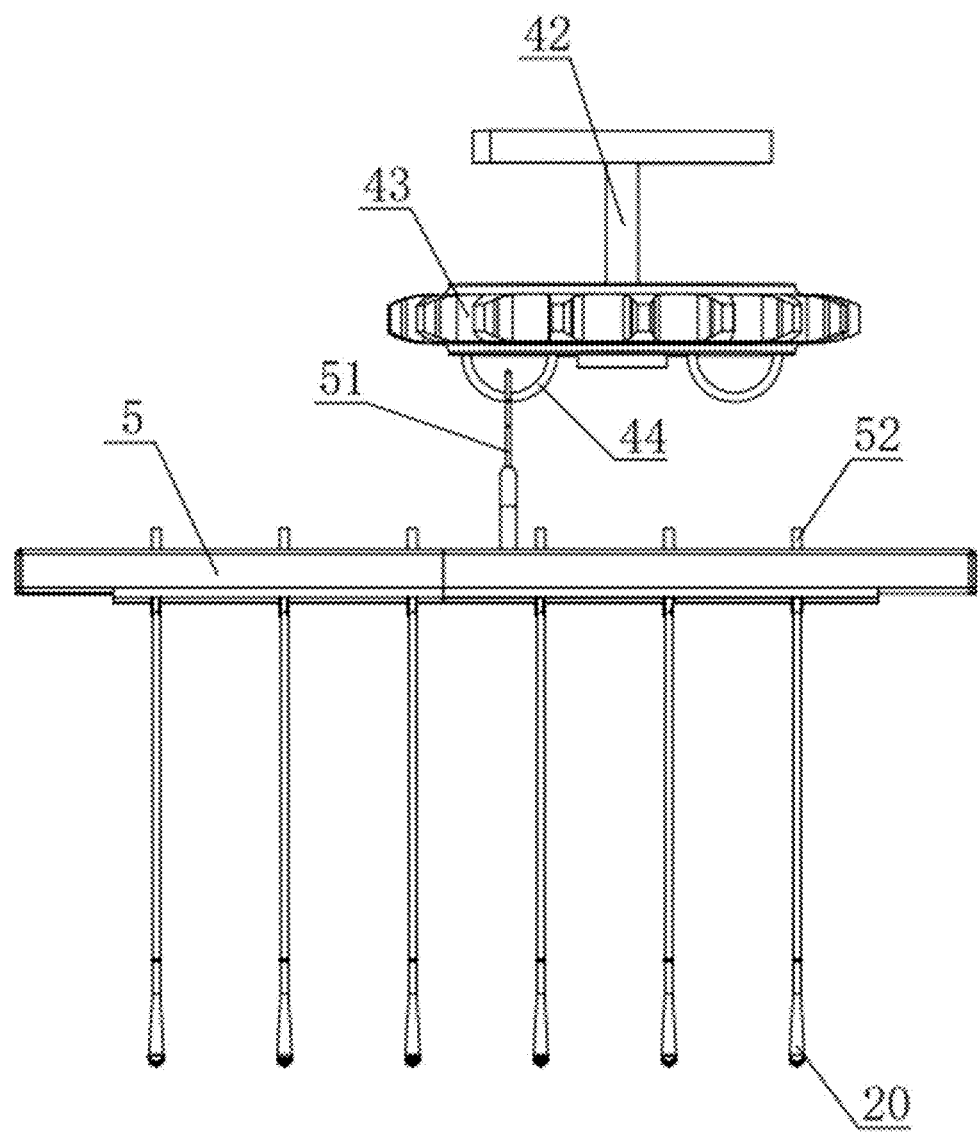
FIG. 8 is a front view of FIG. 7.
Figure 9:
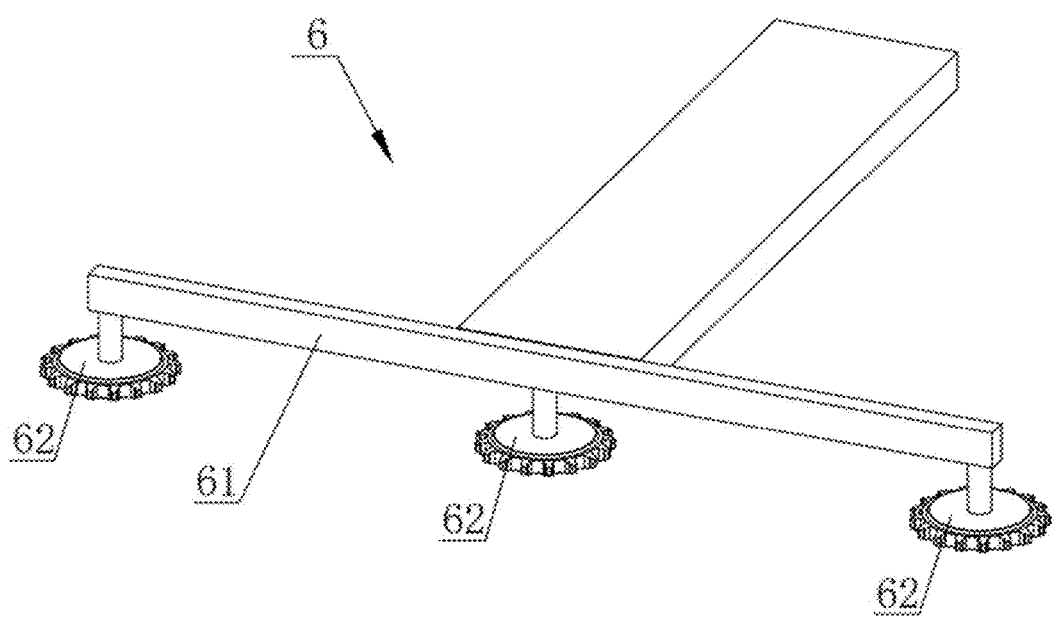
FIG. 9 is a perspective diagram of a fixing frame.

As shown in FIG. 2, several shaft rods 42 are fixed to the conveying drag chain 4 at a uniform interval. As shown in FIG. 2 and FIG. 8, each shaft rod 42 can at a lower end part thereof be rotatably connected with a rotation gear 43, and a semi-circular hanging ring 44 vertically extends downwards from a bottom surface of the rotation gear 43. As shown in FIG. 3, FIG. 4, FIG. 6 and FIG. 9, a fixing frame 6 is fixed to a center of the inner surface of the front side of the flocking box 1 and extends in a direction towards the conveying drag chain 4. Several fixed gears 62 are fixedly arranged on a frame rod 61 at an inner side of the fixing frame 6 at intervals, in which the frame rod 61 is parallel to the conveying drag chain 4. A height position of each fixed gear 62 matches with a height position of respective rotation gear 43, and when each rotation gear 43 follows the conveying drag chain 4 to advance to the position of respective fixed gear 62, the rotation gear 43 is meshed with the respective fixed gear 62, and the rotation gear 43 rotates around the shaft rod 42.

Figure 7:
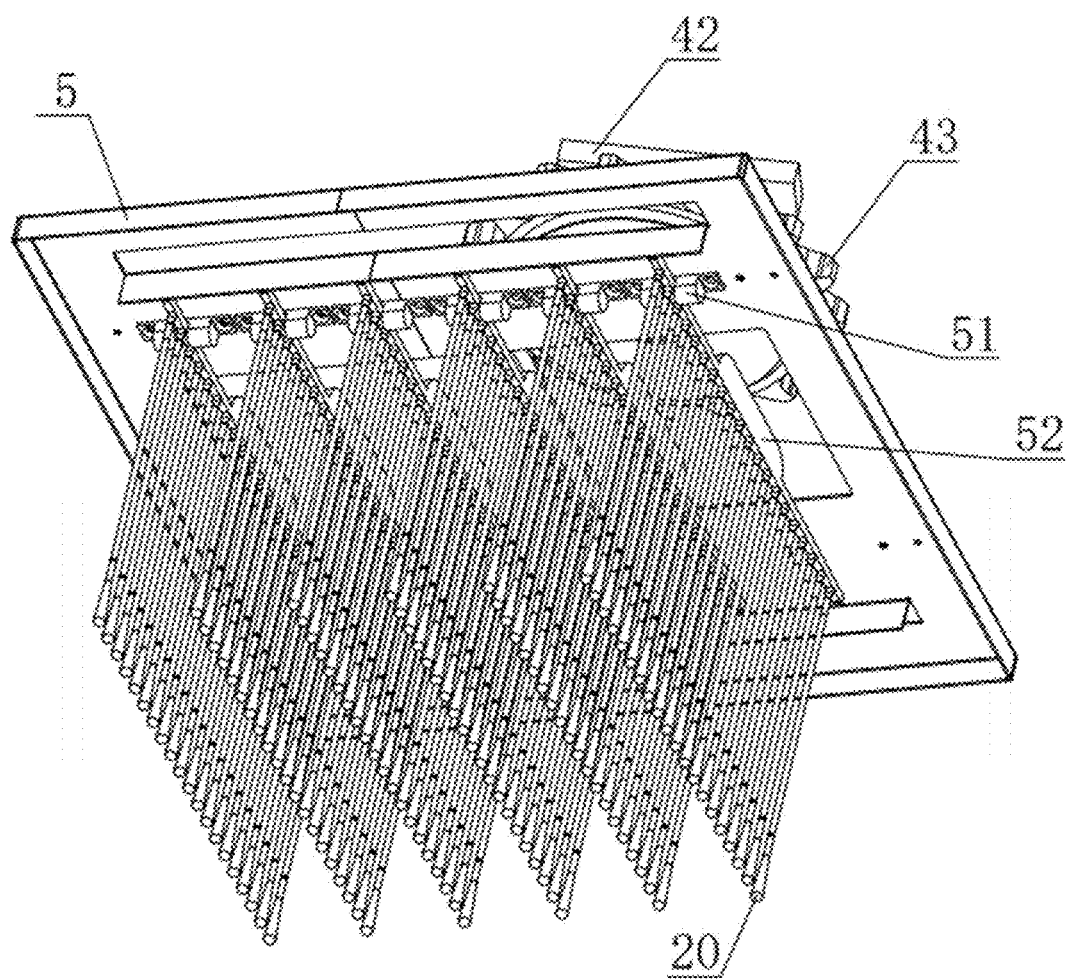
FIG. 7 is a schematic structural diagram showing a swab hanger is connected to a rotation gear.

As shown in FIG. 7 and FIG. 8, a hook 51 extends upward vertically from a center of a top surface of the swab hanger 5. The swab hanger 5 can be hung on the hanging ring 44 of the rotation gear 43 by the hook 51, and the operation is simple and convenient. Several hanging plates 52 are arranged on the swab hanger 5 at a uniform interval, and two ends of each hanging plate 52 are fixed to a bottom surface of the swab hanger 5 through a fixing groove 53, and several swab sticks 20 can be suspended from each hanging plate 52. During flock blowing, the swab hanger 5 can rotate along with the rotation gear 43, such that each surface of the swab stick 20 can be blown by the lateral blower 7, in order that the flocks can fall and adhere to the surface of the swab stick 20 more uniformly, creating better flocking effect.

Figure 10A:
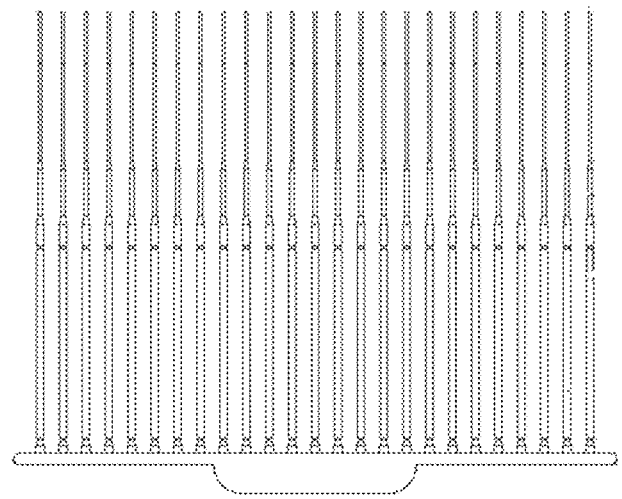
FIG. 10A to FIG. 10F are schematic structure diagrams of various swab sticks.
Figure 10B:
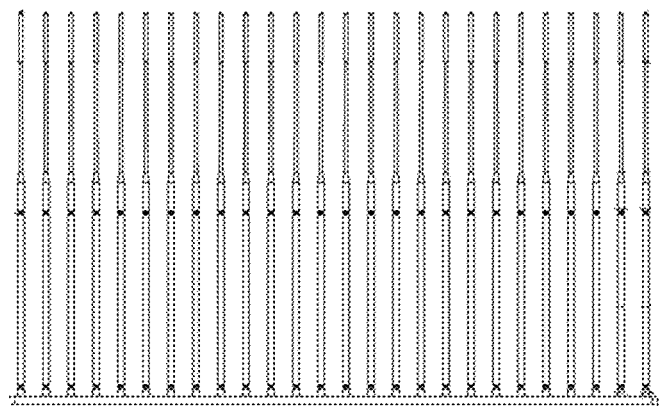
Figure 10C:
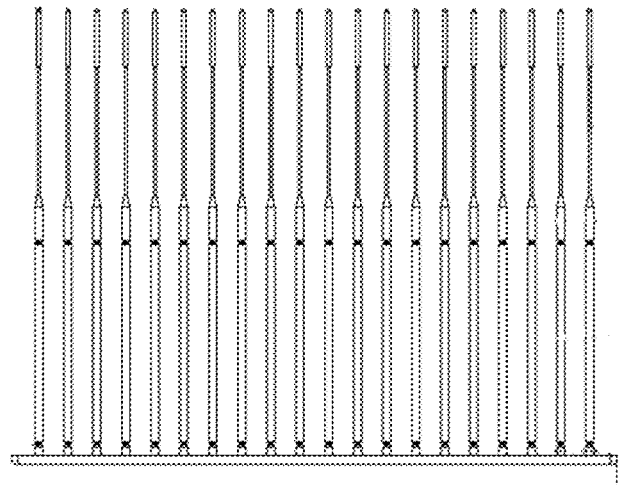
Figure 10D:
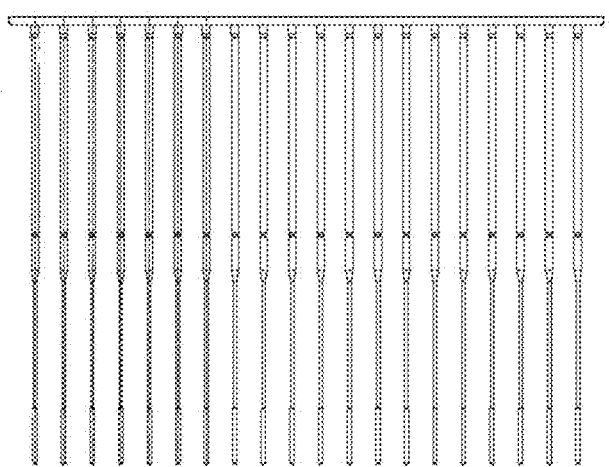
Figure 10E:
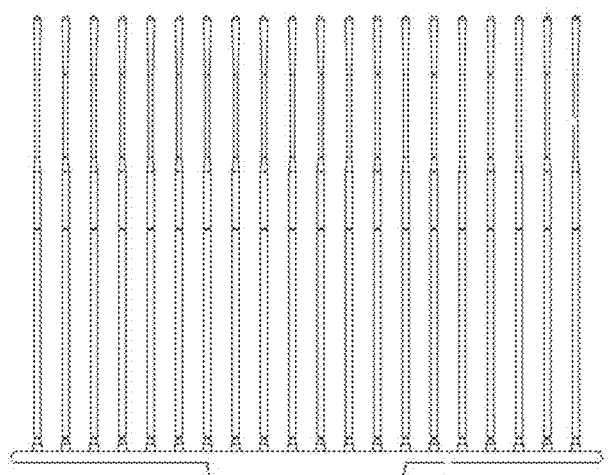
Figure 10F:
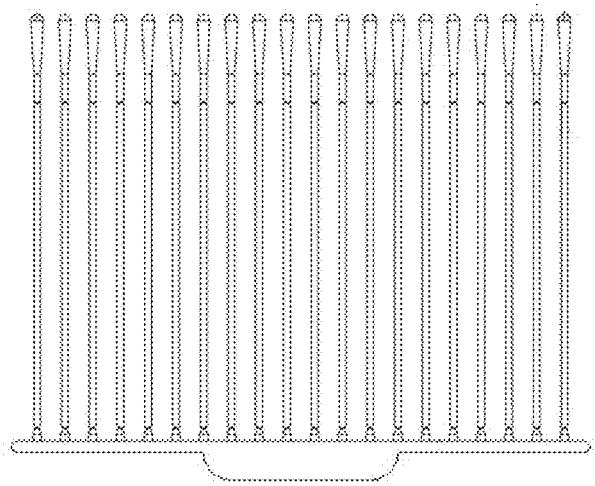

The present disclosure is applicable to the swab sticks 20 of various shapes, different lengths, and break points. Six different shapes of swab sticks 20 as shown in FIG. 10A to FIG. 10F may all be flocked using the present disclosure, in which nasal swabs are shown in FIG. 10A to FIG. 10E, and a throat swab is shown in FIG. 10F.

The specific process for performing flock blowing and flocking on the swab stick 20 by using the present disclosure mainly includes the following steps:

I. hanging and fixing several swab sticks 20 that need to be flocked to a swab hanger 5 firstly;

II. performing plasma treatment on lower end heads of the swab sticks 20 on the swab hanger 5;

III. performing gluing and spin coating treatment on the lower end heads of the swab sticks 20 on the swab hanger 5 in sequence, after the plasma treatment;

IV, hooking the swab hanger 5 to a hanging ring 44 at a bottom surface of a rotation gear 43 of a conveying drag chain 4, after completing the spin coating treatment;

V. starting a first motor 9, and driving the conveying drag chain 4 by the first motor 9 to move, so that the conveying drag chain 4 conveys the swab hanger 5 forward towards a flocking box 1;

VI. pouring flocks on a filter 2, generating friction on the flocks through back-forth movement of a sweeping plate 3, so that the flocks can be fallen into a lower cavity of the flocking box 1 under the action of gravity after the flocks are filtered by the filter 2;

VII. blowing the flocks up by lateral blowers 7 and a vertical blower 8 in the flocking box 1, so that the flocks can be uniformly fallen and adhered to the lower end heads of the swab sticks 20;

VIII. conveying the swab sticks 20 to an outside with the swab hangers 5 by the conveying drag chain 4, after the flock blowing is completed;

IX. drying the swab sticks 20 having been experienced the flock blowing;

X. taking down the swab sticks 20 from the swab hanger 5, after the drying is completed, to complete the flocking process.

Figure 11A:
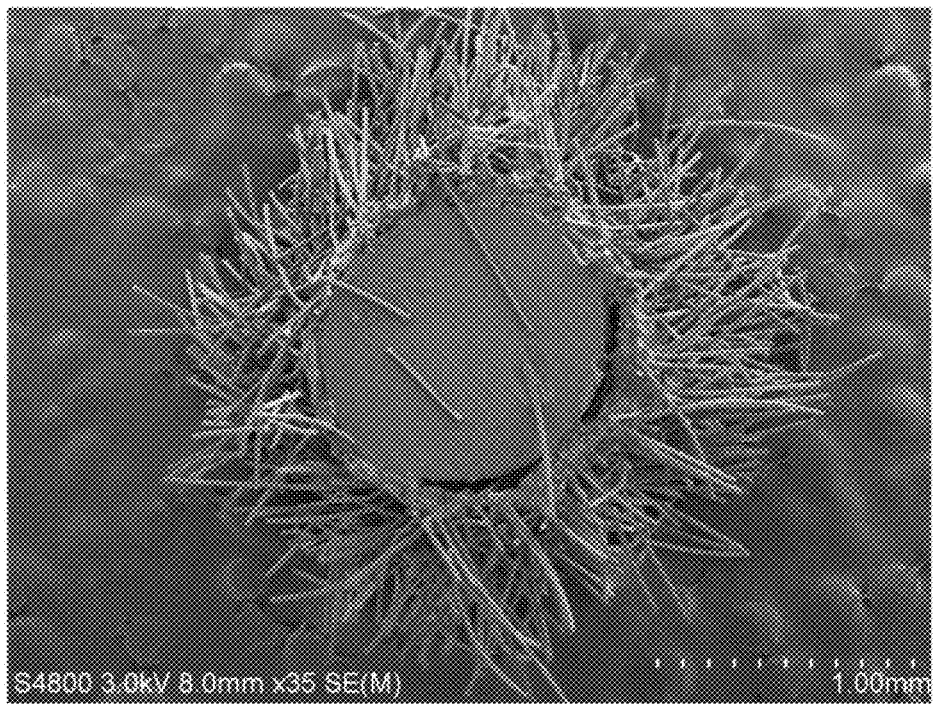
FIG. 11A is a cross-sectional view of a swab after being flocked in accordance with the present disclosure under an electron microscope.
Figure 11B:
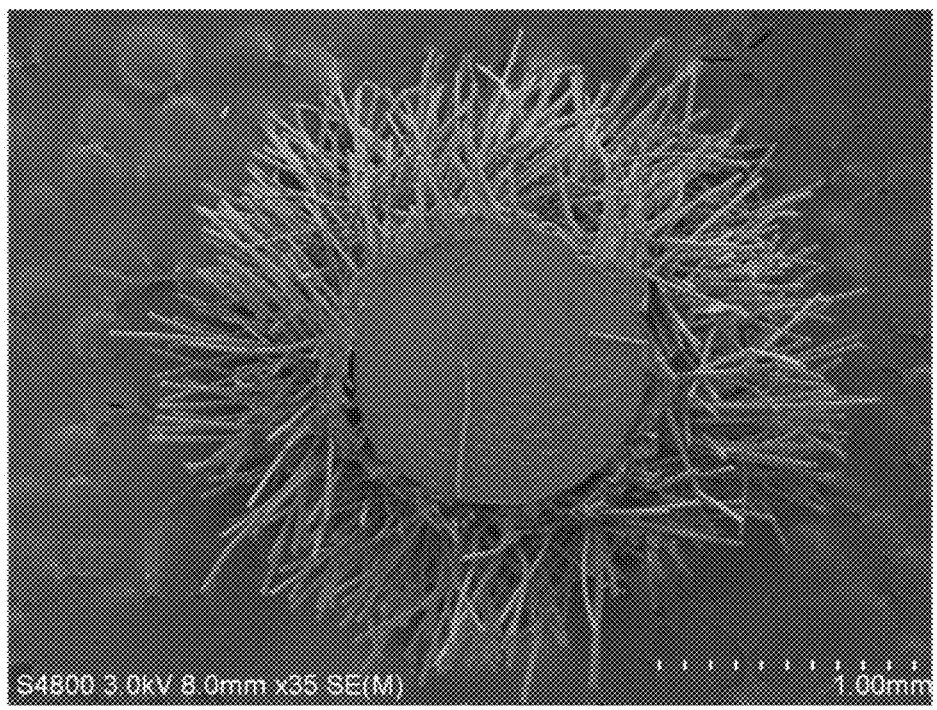
FIG. 11B is a cross-sectional view of an electrostatically flocked swab under an electron microscope.
Figure 12A:
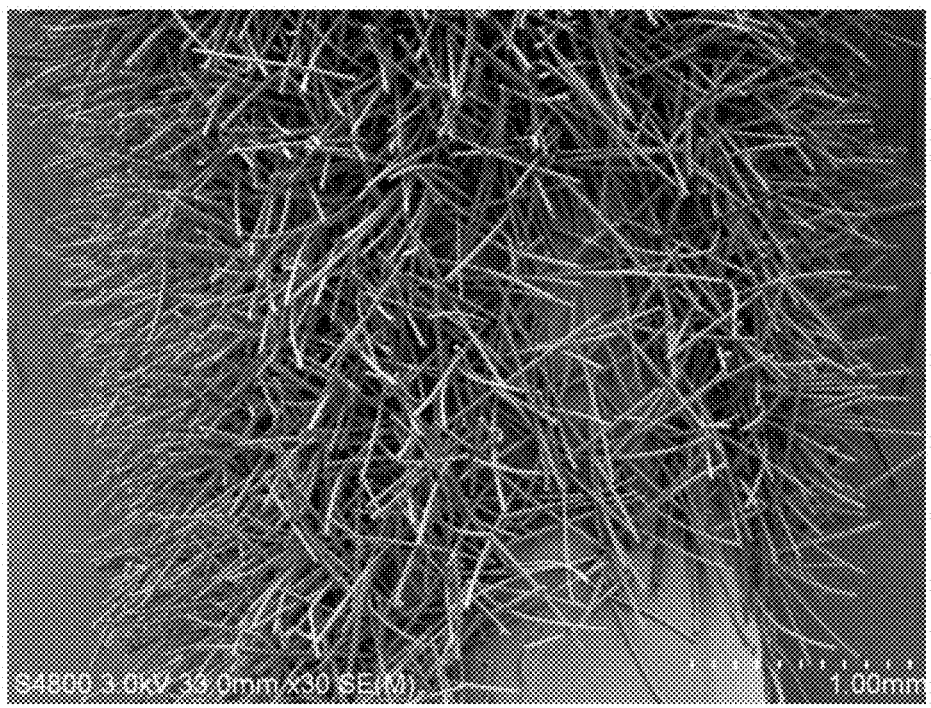
FIG. 12A to FIG. 12G are enlarged views of a nasal swab after plasma treatment under the electron microscope.
Figure 12B:
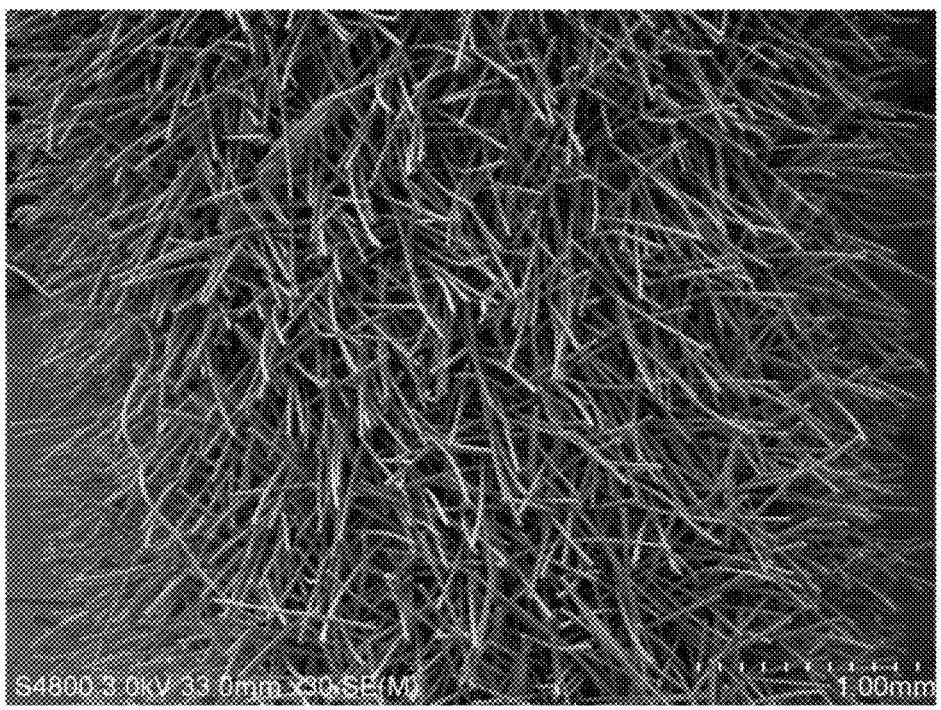
Figure 12C:
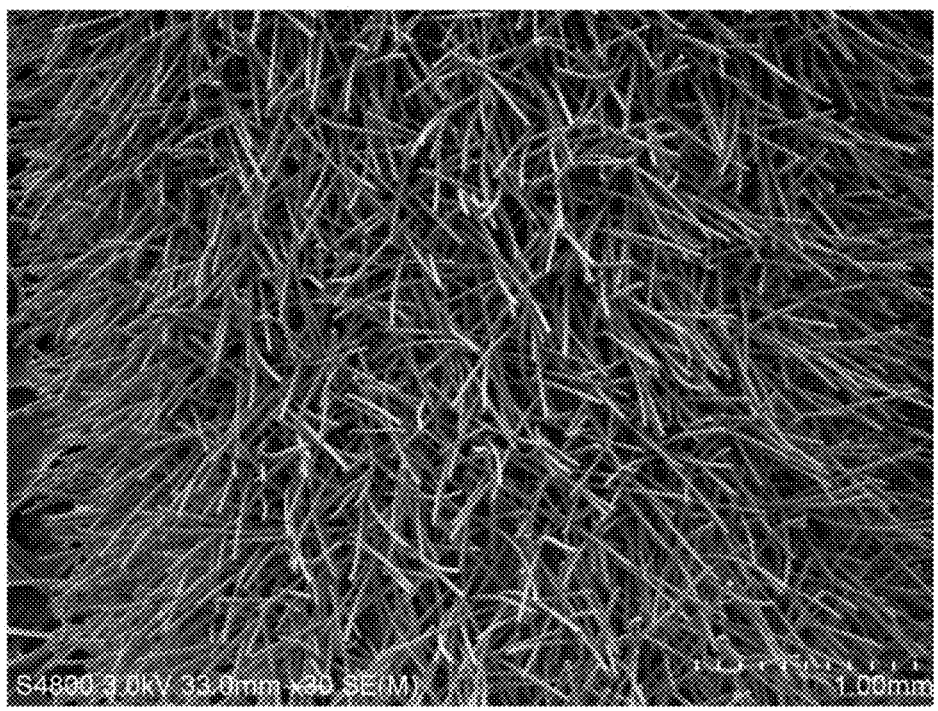
Figure 12D:
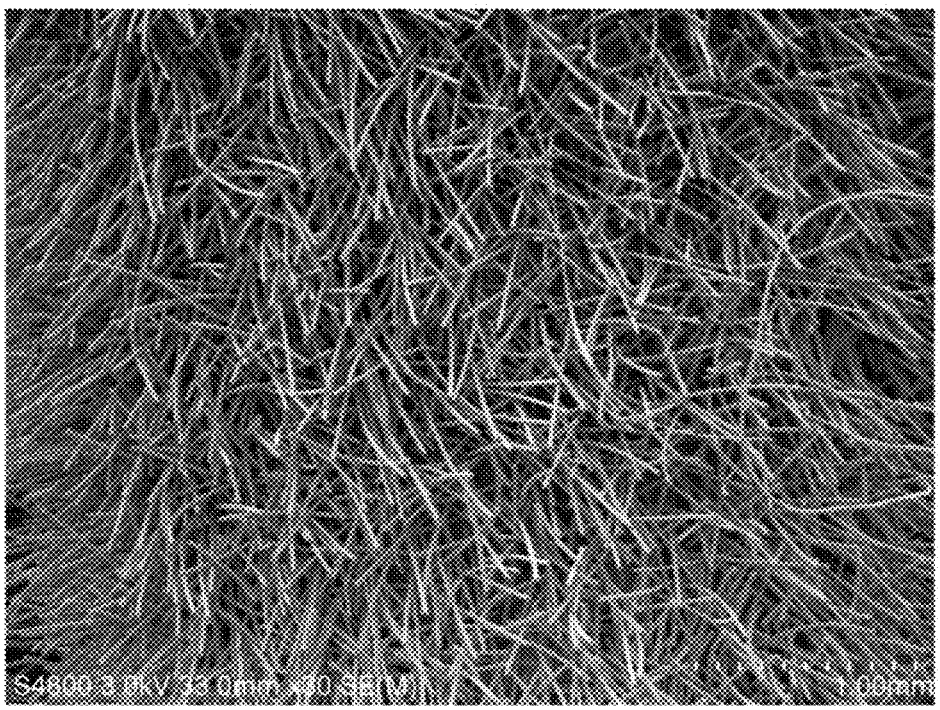
Figure 12E:
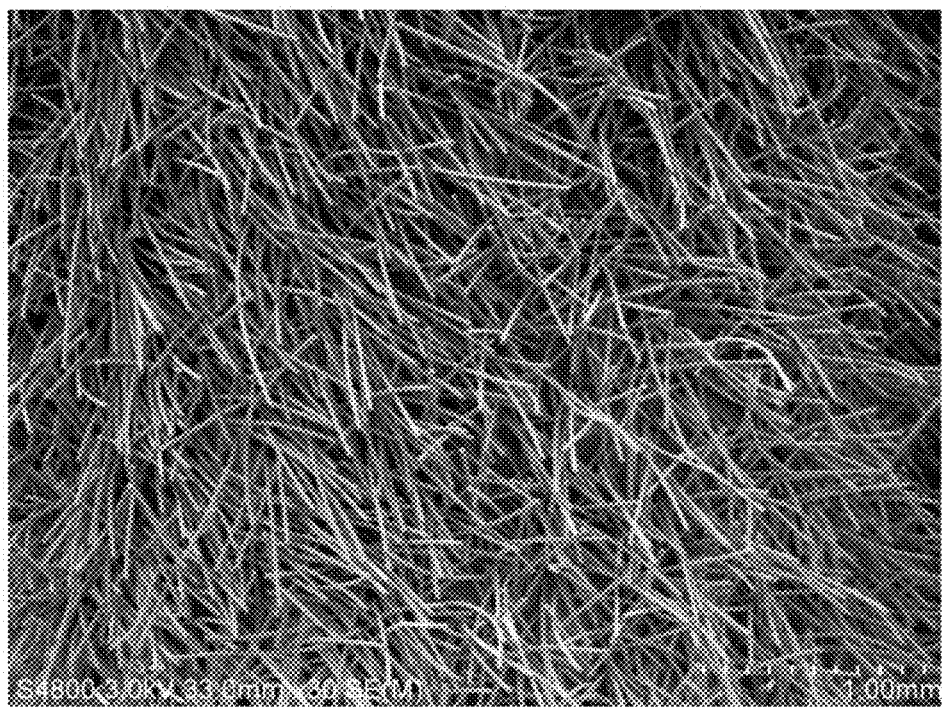
Figure 12F:
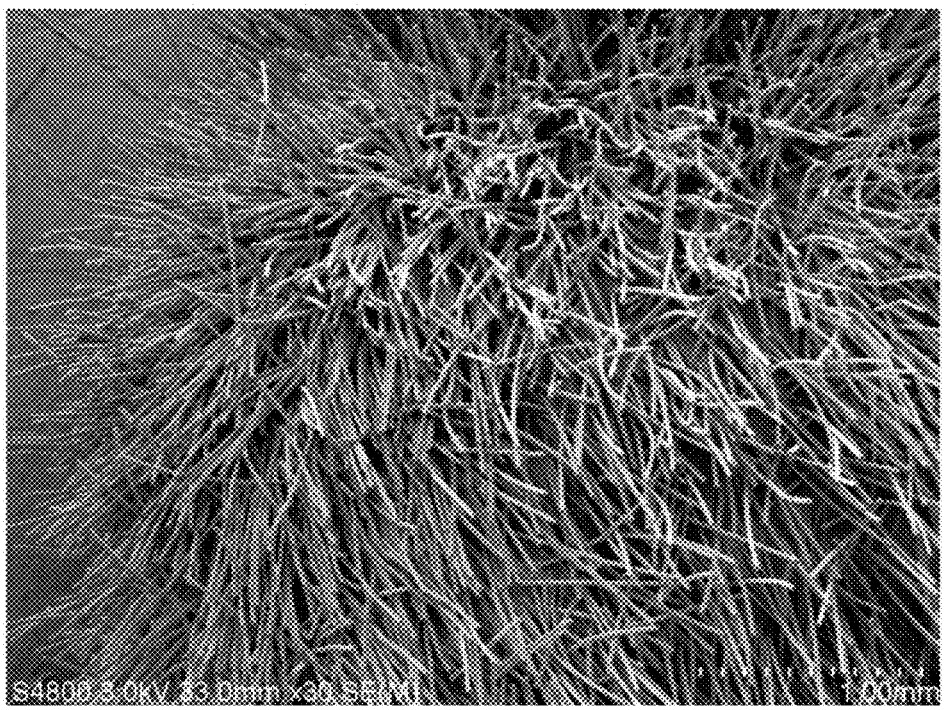
Figure 12G:
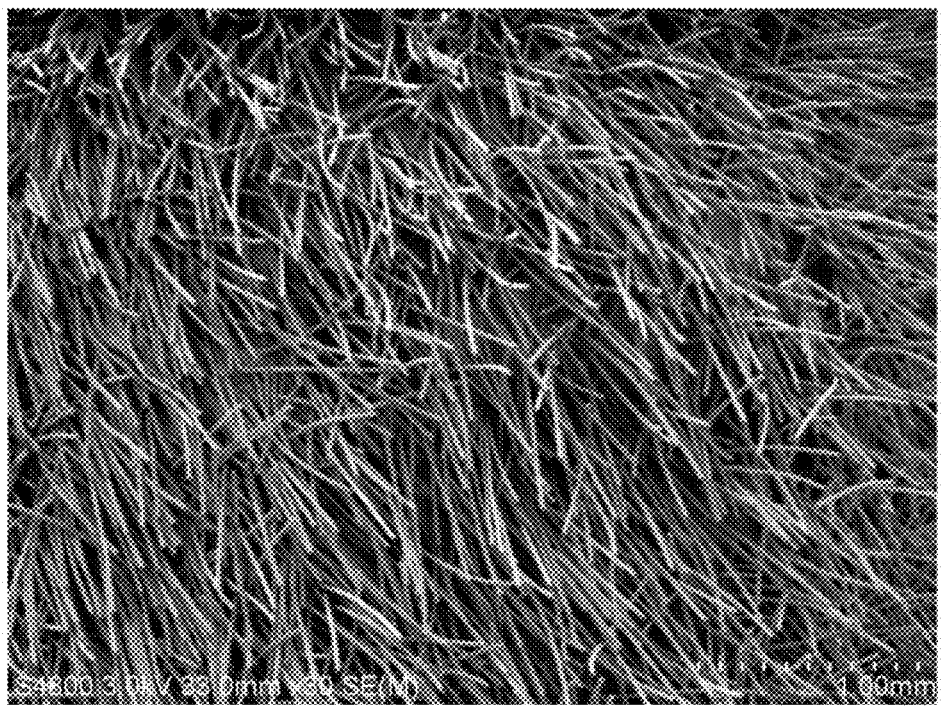
Figure 13A:
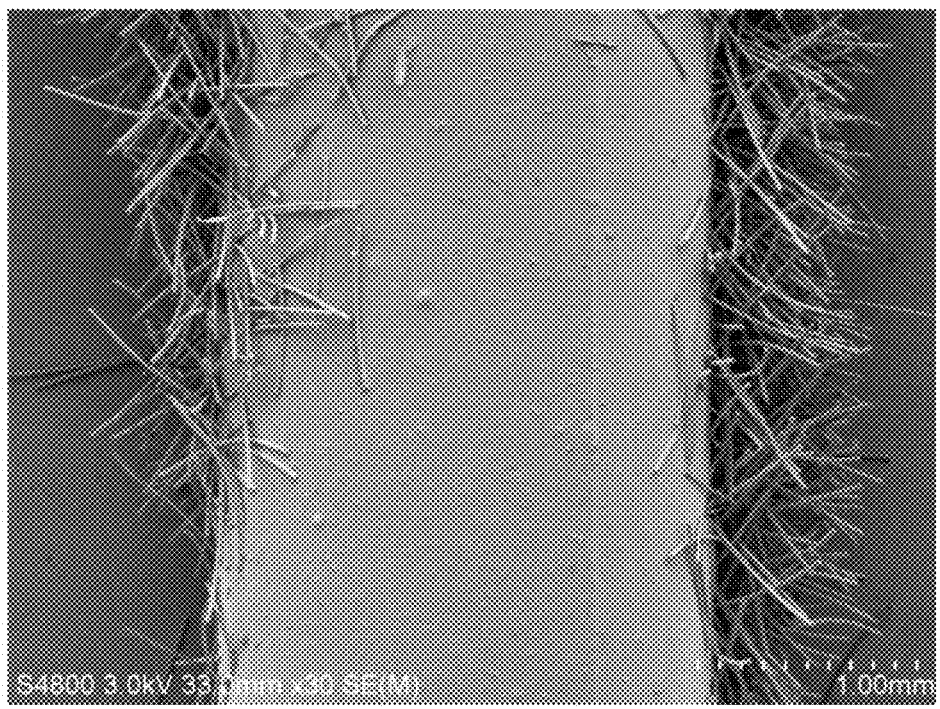
FIG. 13A to FIG. 13G are enlarged views of a nasal swab without plasma treatment under the electron microscope.
Figure 13B:
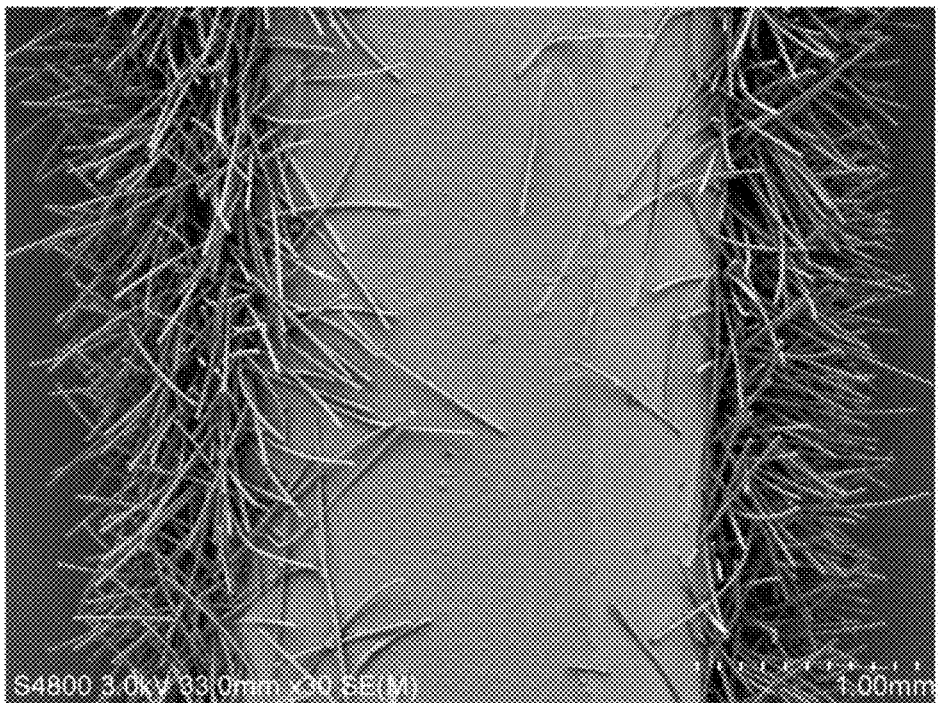
Figure 13C:
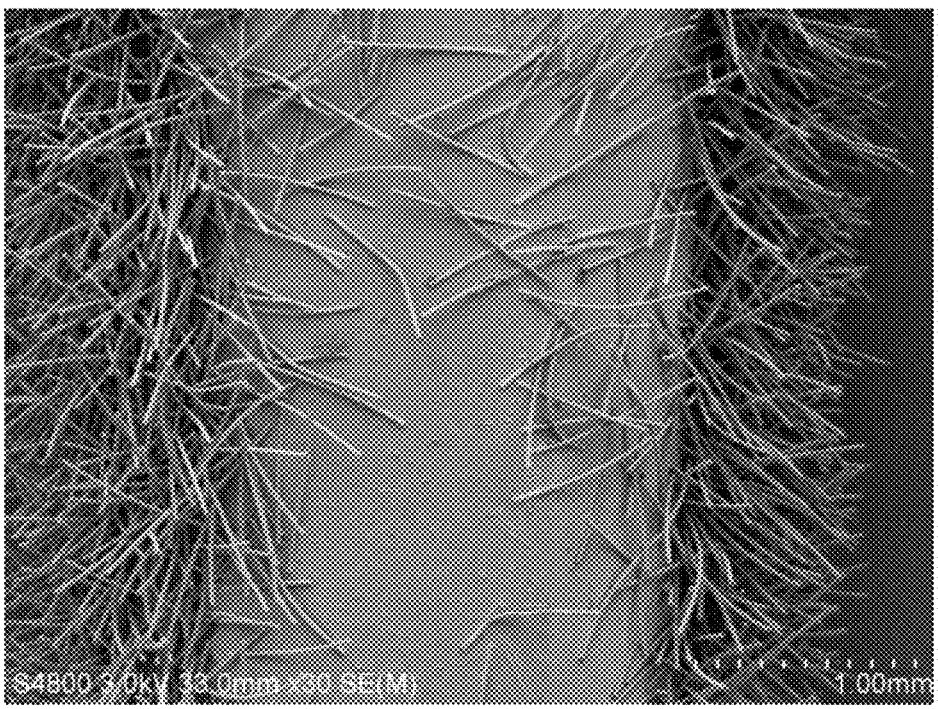
Figure 13D:
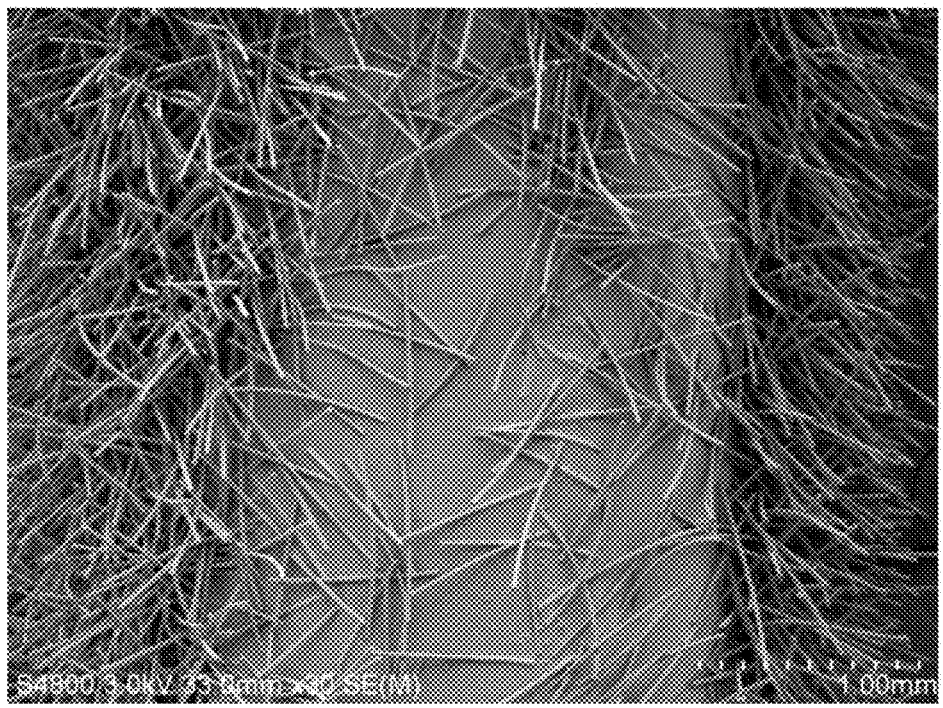
Figure 13E:
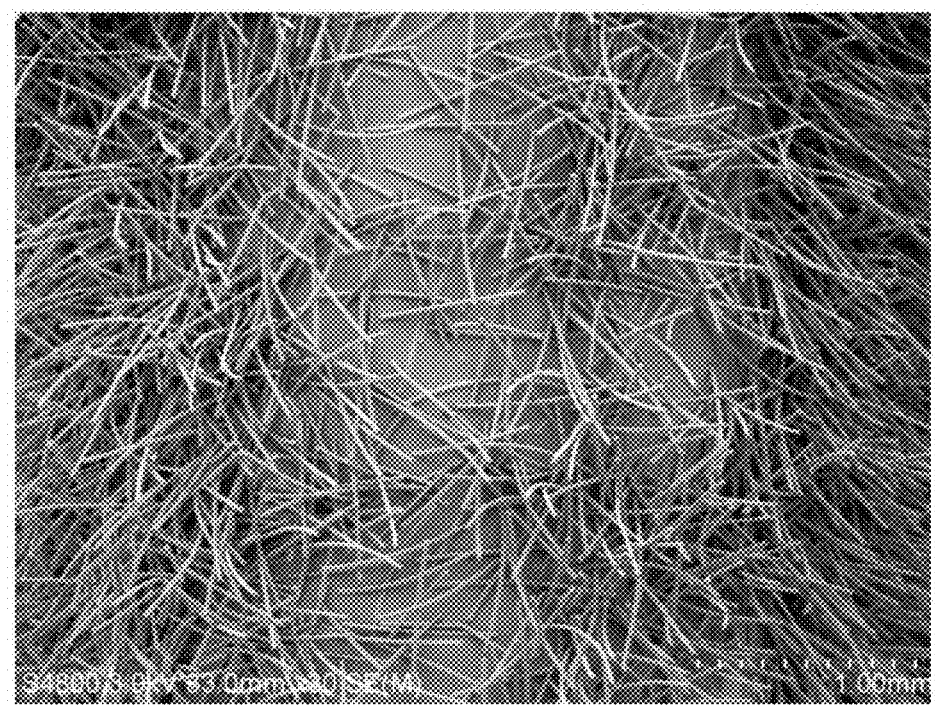
Figure 13F:
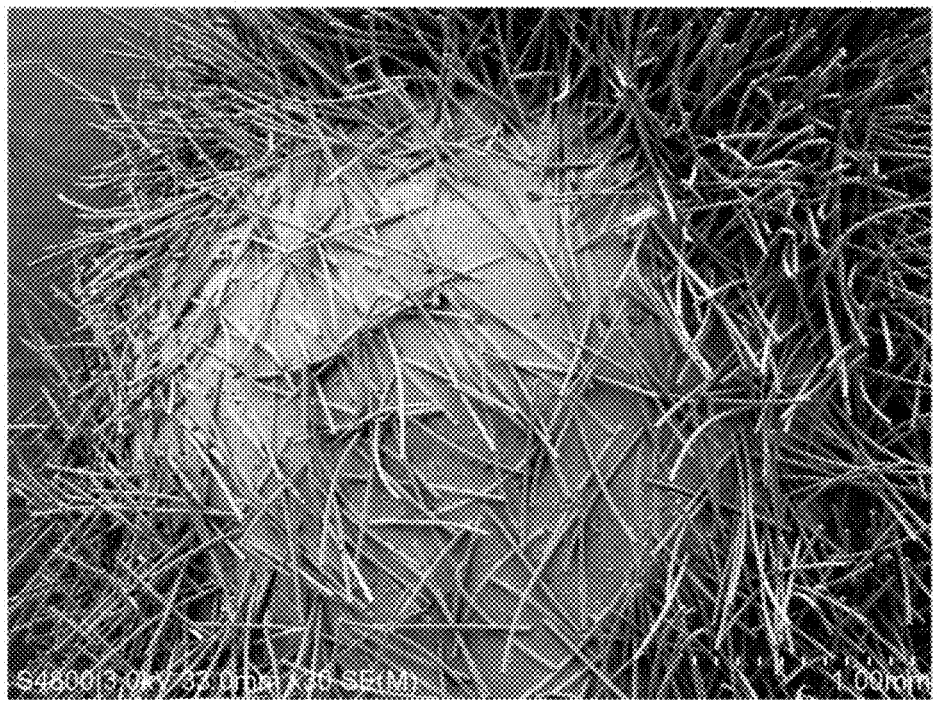
Figure 13G:
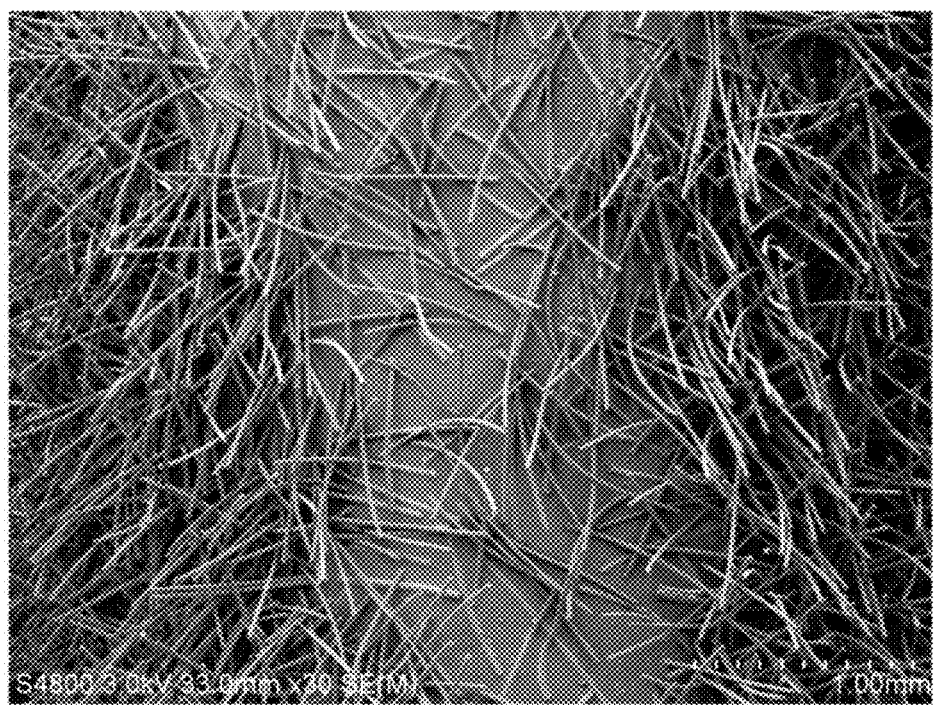
Figure 14A:
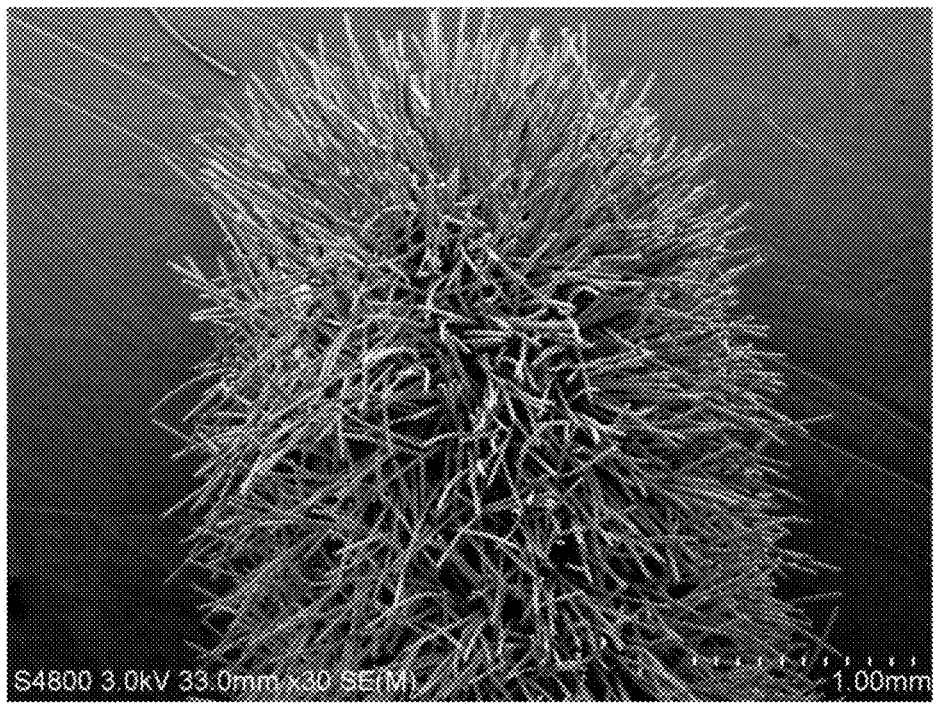
FIG. 14A to FIG. 14E are enlarged views of a throat swab after plasma treatment under the electron microscope.
Figure 14B:
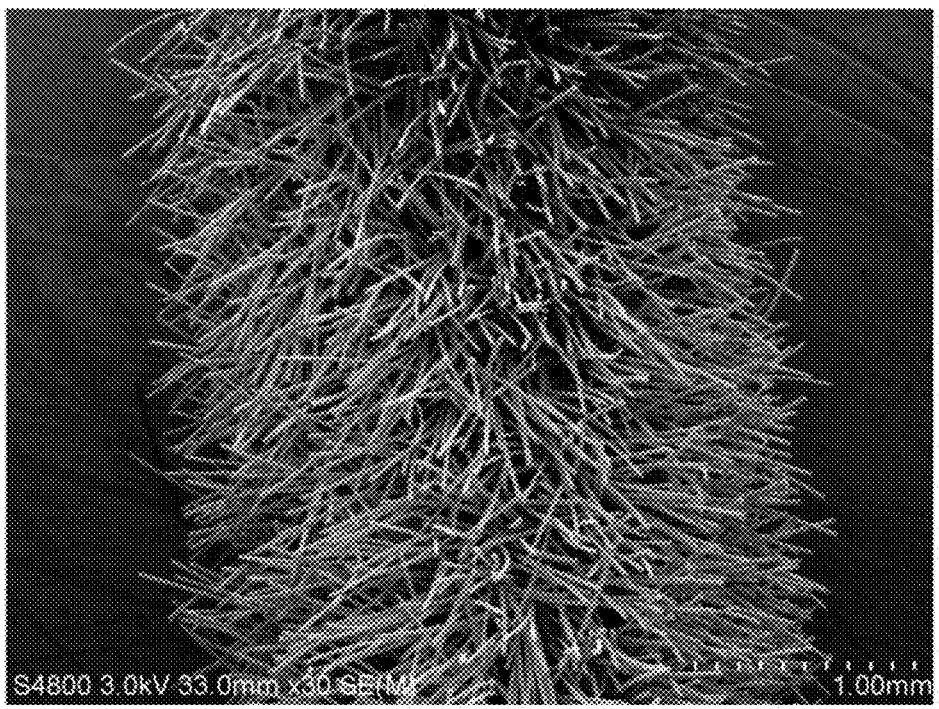
Figure 14C:
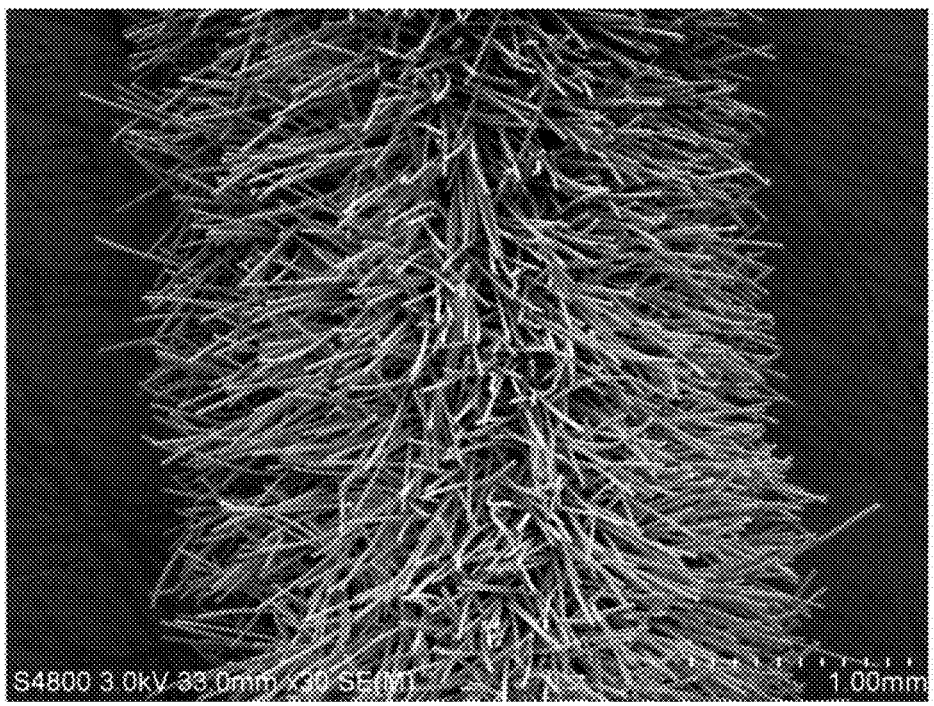
Figure 14D:
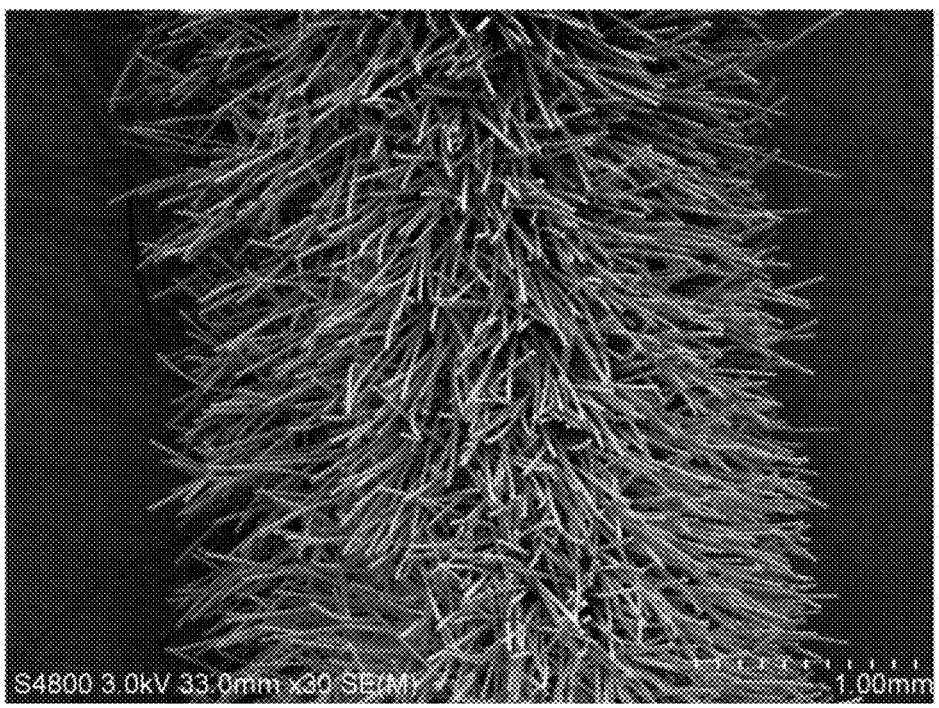
Figure 14E:
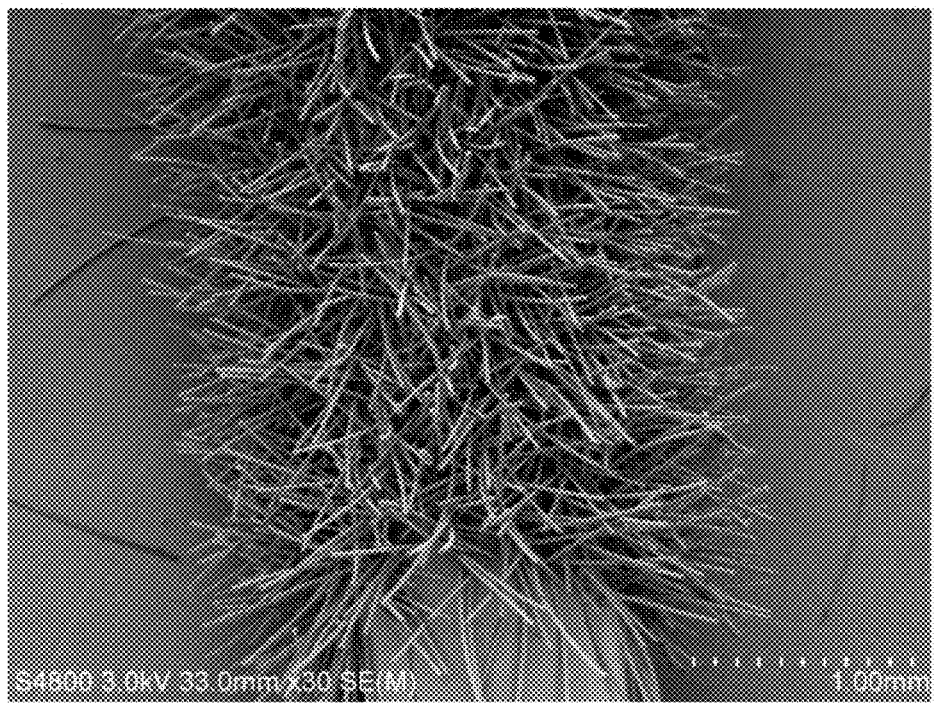
Figure 15A:
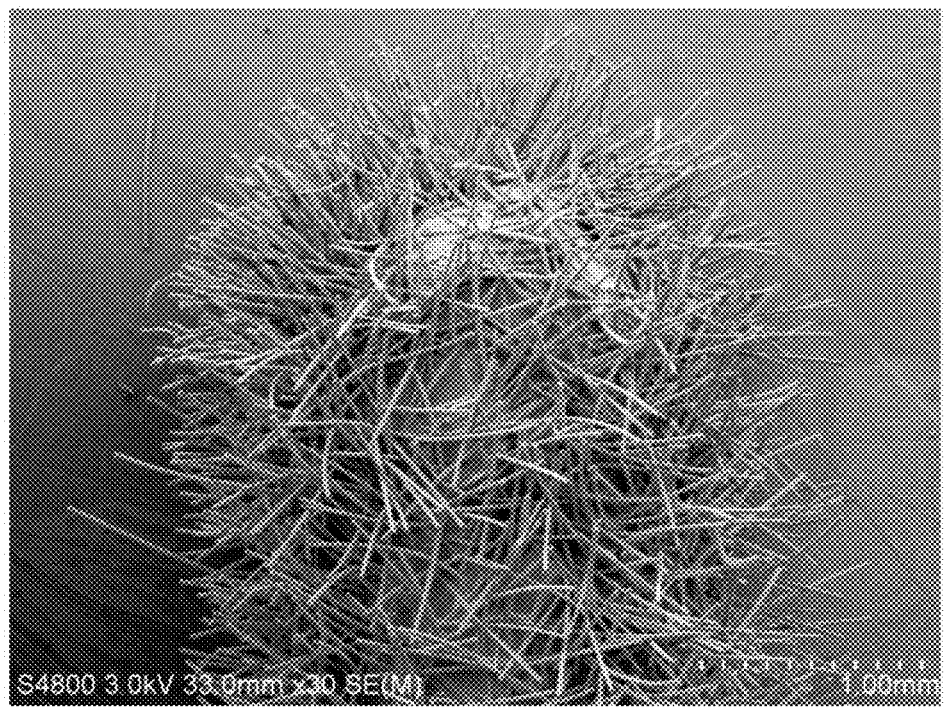
FIG. 15A to FIG. 15E are enlarged views of a throat swab without plasma treatment under the electron microscope.
Figure 15B:
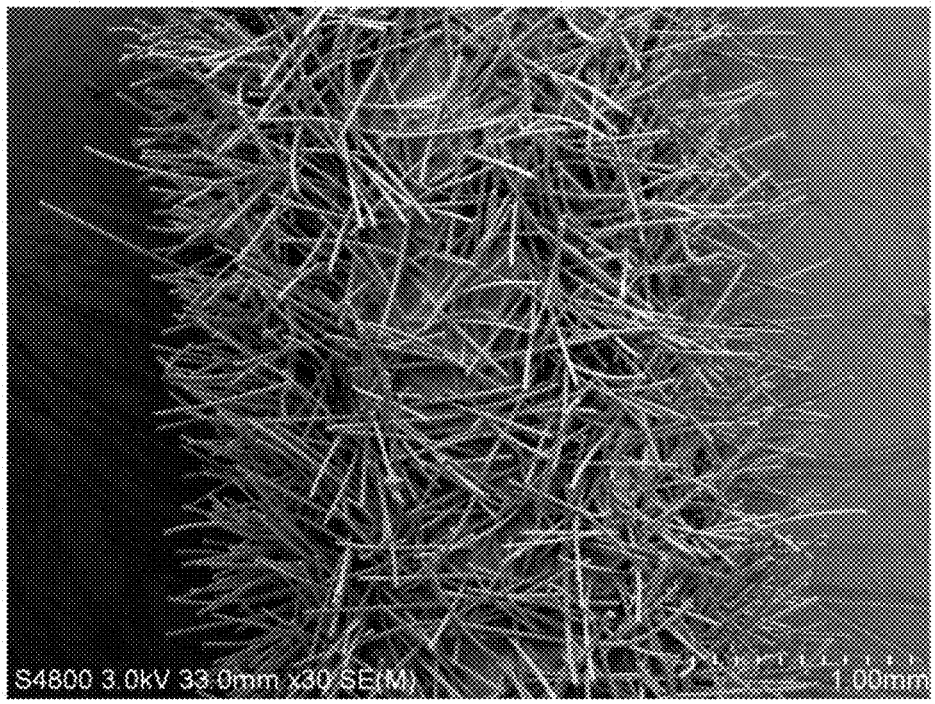
Figure 15C:
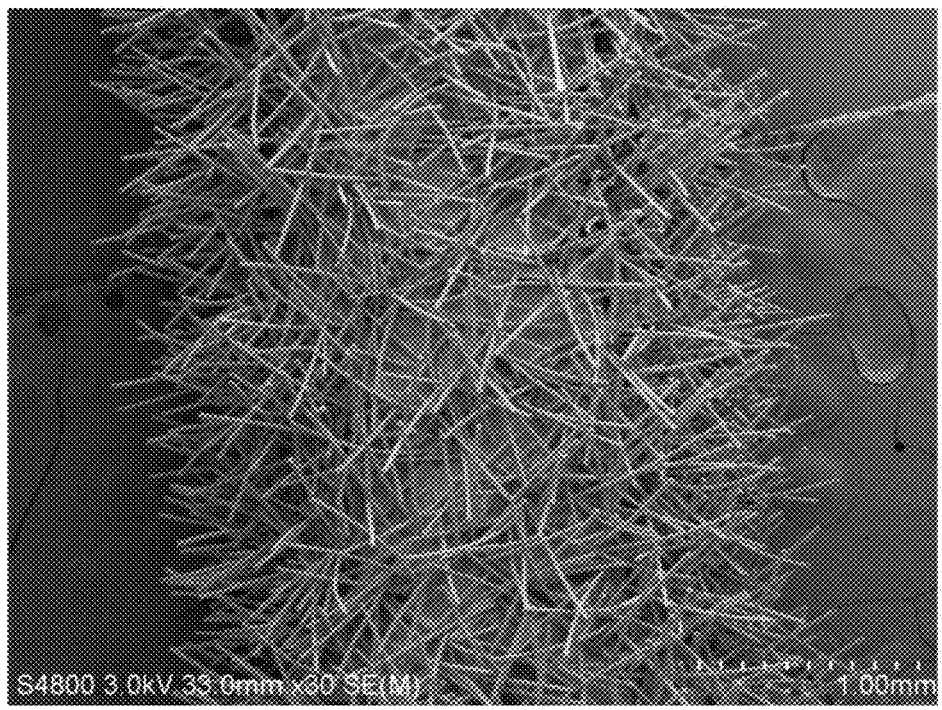
Figure 15D:
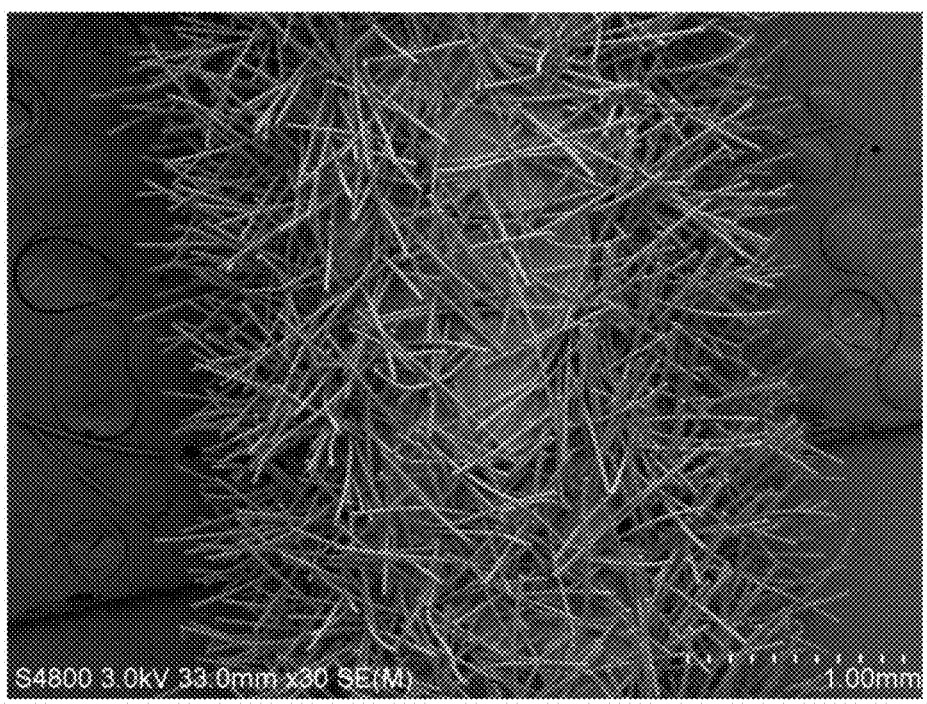
Figure 15E:
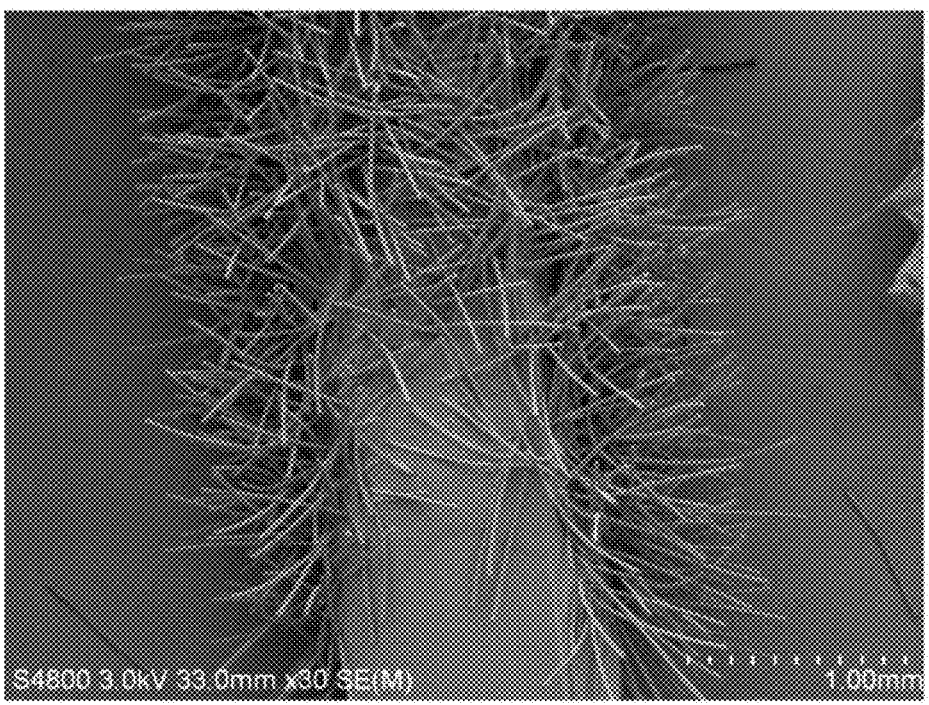

In FIG. 11A, a cross-sectional view of a swab stick 20 under an electron microscope after the flocking of the swab stick 20 is completed by using the present disclosure is shown. As can be seen from the figure, the flocks are uniformly adhered to the surface of the swab stick 20, the flocking effect is good, and the performance requirement of the swab can be satisfied. Compared with a cross-sectional view of an electro-statically flocked swab stick 20 under the electron microscope in FIG. 11B, it is observed that the flock adhesion and the adhesion consistency of the swab produced in accordance with the present disclosure have no great difference from those of the electrostatically-flocked swab.

The swab stick 20 may also have different flocking effects with and without plasma treatment before flocking: (1) FIG. 12A to FIG. 12G show enlarged views of various parts of a nasal swab after plasma treatment under an electron microscope, and FIG. 13A to FIG. 13G show enlarged views of corresponding parts of a nasal swab without plasma treatment under the electron microscope; (2) FIG. 14A to FIG. 14E show enlarged views of various parts of a throat swab after plasma treatment under the electron microscope, and FIG. 15A to FIG. 15E show enlarged views of corresponding parts of a throat swab without plasma treatment under the electron microscope. As can be seen from the above comparison figures, after the swab without plasma treatment is flocked, there is little flock and poor adhesion, while after the swab with plasma treatment is flocked, there is uniform flock coverage and better adhesion.

The swab stick 20 may also have different flocking effects with and without spin coating treatment before flocking: (1) FIG. 16A1 to FIG. 16A4 are enlarged views of various parts of a nasal swab after spin coating treatment under the electron microscope, and FIG. 16B1 to FIG. 16B3 show cross-sectional views of a nasal swab after spin coating treatment under the electron microscope; (2) FIG. 17A1 to FIG. 17A4 show enlarged views of various parts of a nasal swab without spin coating treatment under the electron microscope, and FIG. 17B1 to FIG. 17B3 are cross-sectional views of corresponding parts of a nasal swab without spin coating treatment under the electron microscope. As can be seen from the above comparison figures, after the swab without spin coating treatment is flocked, there is little flock and poor adhesion, while after the swab with spin coating treatment is flocked, there is uniform flock coverage and better adhesion.

By means of the present disclosure, a flock density of flocking is in a range between 3.8 to 6.0 Dtex, and a flock length is in a range between 0.4 to 0.6 mm. Preferably, the flock density is 4.2 Dtex, and the flock length is 0.5 mm. The following are test comparison results of corresponding tests on the swabs after being flocked with two different flock densities:

1) Test materials were prepared at first:

A). two swabs: (1) a testing swab (4.2 Dtex*0.5 mm); (2) a compared production swab (3.3 Dtex*0.8 mm);

B). two preservation solution: (1) ITM (Inactivation Transport medium) inactivated preservation solution; and (2) VTM (Viral Transport Medium) non-inactivated preservation solution; and C). armored RNA (ribonucleic acid) ($10^6$ copies/ml) diluent.

2) Specific experimental steps were described as follows:

S1: sample treatment.

S11: experimental group treatment, wherein 50 μL armored RNA diluent droplets were dripped onto two swab heads, and after standing for 5 seconds, the two swab heads were transferred into 1 mL of ITM inactivated preservation solution and 1 mL VTM non-inactivated preservation solution, respectively, and after uniformly mixing by vortex, 200 μL preservation solutions were taken for nucleic acid extraction, respectively;

S12: compared group treatment, wherein 50 μL armored RNA diluent were directly added into 1 mL ITM inactivated preservation solution and 1 mL VTM non-inactivated preservation solution, and after uniformly mixing by vortex, 200 μL preservation solutions were taken for nucleic acid extraction, respectively;

S2: sample extraction, wherein an AU17012 magnetic bead method viral DNA/RNA extraction kit was used to perform the sample extraction.

S21: pre-adding reagent, wherein the following reagents (listed in Table 1) were added in a 96-well deep well plate:

TABLE 1

| Serial number | Reagent name | Number of deep well plate | Reagent pack quantity |
| --- | --- | --- | --- |
| 1 | Virus lysis buffer VL2 | 1 | 400 μL |
| 2 | Virus magnetic bead BB | 2 | 600 μL |
| 3 | Virus magnetic bead | 2 | 10 μL |
| 4 | Wash buffer (Buffer A) | 3 | 500 μL |
| 5 | Wash Buffer WB | 4 | 700 μL |
| 6 | Elution buffer | 6 | 50 μL |

S22: sample injection, wherein 200 μL preservation solution samples were injected;

S23: program setting of nucleic acid extractor, wherein the details were as follows (listed in Table 2):

TABLE 2

| (AU17012) | | | | | | | | | |
| --- | --- | --- | --- | --- | --- | --- | --- | --- | --- |
| Step | Well position | Waiting time (min) | Mixing time (min) | Mixing speed | Temperature time (min) | Temperature (° C.) | Magnetic suction Time (s) | Magnetic suction speed | Volume |
| 1 | 2 | 0 | 0 | Four | 0 | 0 | 30 | Low speed | 600 |
| 2 | 1 | 0 | 40 | Four | 0 | 0 | 30 | Low speed | 600 |
| 3 | 3 | 0 | 20 | Four | 0 | 0 | 30 | Low speed | 450 |
| 4 | 4 | 0 | 20 | Four | 0 | 0 | 30 | Low speed | 700 |
| 5 | 6 | 0 | 40 | Three | 0 | 0 | 30 | Low speed | 200 |
| 6 | 2 | 0 | 5 | Three | 0 | 0 | 0 | Low speed | 500 |

S24: After the end of program operation, taking 5 μL nucleic acid in each of 6/12 well positions for QPCR (Real-Time Fluorescent Quantitative Polymerase Chain Reaction) amplification;

S3: sample monitoring, wherein QPCR was used to perform real-time fluorescence quantitative analysis:

Configuring Boiri qRT-PCR Amplification System (Table 3):

TABLE 3

| Reagent | Usage amount |
| --- | --- |
| 5× Neoscript Fast RT Buffer | 5 μl |
| 25× Neoscript Fast RTase/UNG mix | 1 μl |
| Primer 1 | 0.5 μl |
| Primer 2 | 0.5 μl |
| TaqMan Probe | 0.5 μl |
| ddH2O | 12.5 μl |
| Template RNA | 5 μl |
| Total | 25 μl |

Analysis Program (Table 4):

TABLE 4

| Step | Number of cycles | Temperature (° C.) | Time | Fluorescence channel |
|---|---|---|---|---|
| 1 | 1 | 55 | 15 min | |
| 2 | 1 | 95 | 30 sec | |
| 3 | 45 | 95 | 10 sec | |
| | | 58 | 30 sec | Collecting FAM/HEX Fluorescence |

3) Experimental results were as follows (Table 5):

TABLE 5

| Type of swab | Type of preservation solution | Ct value | Mean value |
|---|---|---|---|
| Compared swab | ITM | 30.56 | 30.57 |
| | | 30.42 | |
| | | 30.72 | |
| | VTM | 30.61 | 30.71 |
| | | 30.74 | |
| | | 30.77 | |
| Test swab | ITM | 30.28 | 30.25 |
| | | 30.3 | |
| | | 30.16 | |
| | VTM | 30.54 | 30.52 |
| | | 30.35 | |
| | | 30.66 | |
| Compared group | ITM | 29.87 | 29.92 |
| | | 29.99 | |
| | | 29.9 | |
| | VTM | 30.18 | 30.15 |
| | | 30.16 | |
| | | 30.12 | |

4) Analysis of conclusion was as follows:

Difference between Ct values of the two swabs: the Ct mean value difference of ITM=30.57−30.25=0.32; the Ct mean value difference of VTM=30.71−30.52=0.19.

Comparison between Ct value difference of the compared group and Ct value difference of the Test swab:

Compared swab: the Ct mean value difference of ITM=30.57−29.92=0.65; the Ct mean value difference of VTM=30.71−30.15=0.56;

Test swab: the Ct mean value difference of ITM=30.25−29.92=0.33; the Ct mean value difference of VTM=30.52−30.15=0.37.

An evaluation result was described as follows: the calculation of relative expression quantity of a target gene after fluorescent quantitative PCR (polymerase chain reaction) generally adopts $2^{\Delta CT}$ method.

The release effects of the two swabs were compared as follows: the Ct mean value difference of ITM was equal to 0.33, and the release effect of the test swab was $2^{0.33}$=1.25 times that of the compared swab; the Ct mean value difference of VTM=0.19, and the release effect of the test swab was $2^{0.19}$=1.14 times that of the compared swab.

The release efficiency of the two swabs was as follows:

The release efficiency of the compared swab in the ITM was $2^{(-0.65)}$=63.73%, and the release efficiency of the compared swab in the VTM was $2^{(-0.56)}$=67.83%;

The release efficiency of the test swab in the ITM was $2^{(-0.33)}$=79.55%, and the release efficiency of the test swab in the VTM was $2^{(-0.37)}$=77.38%.

As can be seen from the above test results, the test swab has good flocking effect and can satisfy the performance requirements.

According to the present disclosure, the swab stick 20 is flocked in a flock blowing mode, the flocks are uniformly adhered to the surface of the swab stick 20, and the flocking effect is good. During the flocking process, only blowers are required for supplying wind power. Compared with an electrostatic flocking mode, the demand for electric energy is greatly reduced, the power consumption is decreased, the energy consumption is lowered, and the electrostatic effect in the flocking process is also avoided, therefore ensuring the flocking effect and the swab quality.

The above description is an explanation of the present disclosure, not a limitation of the present disclosure. The present disclosure can be modified in any form without departing from the spirit of the present disclosure.

What is claimed is:

1. A swab flocking device, wherein:
a conveying drag chain transversely penetrates through a flocking box, a plurality of swab hangers are arranged on the conveying drag chain at intervals, and the conveying drag chain is connected to a first motor;
a plurality of blowers are arranged at an outer side of the conveying drag chain in the flocking box; and
each of the swab hangers is configure for a swab stick to be hung thereon during flocking, and to be conveyed forwards by the conveying drag chain, and the a plurality of blowers are configured to blow flocks onto an end head of the swab stick; and
wherein:
a plurality of shaft rods are fixed to the conveying drag chain at a uniform interval, and rotation gears are rotatably connected to the shaft rods;
a fixing frame is arranged on an inner surface of the flocking box, a plurality of fixed gears are arranged on a frame rod of the fixing frame at intervals, and a height position of each fixed gear matches with a heigh position of a respective rotation gear; and
when the rotation gears follow the conveying drag chain to advance to positions of the fixed gears, the rotation gears are meshed with the fixed gears.

2. The swab flocking device according to claim 1, wherein the blowers comprise lateral blowers which are respectively arranged around a swab hanger of the plurality of swab hangers that is at a central part of the flocking box, and each lateral blower is configured to laterally blow air towards the swab hanger at the central part of the flocking box.

3. The swab flocking device according to claim 1, wherein the blowers comprise a vertical blower arranged at a center of a bottom of the flocking box and directly facing the conveying drag chain, and the vertical blower is configured to vertically blow air to a swab hanger of the plurality of swab hangers that is at a central part of the flocking box.

4. The swab flocking device according to claim 1, wherein:
a hanging ring is arranged at a bottom surface of each rotation gear; and a hook is arranged on a top surface of each of the swab hangers, and
each of the swab hangers is hung on the hanging ring of each rotation gear by the hook respectively.

5. The swab flocking device according to claim 1, wherein:
a filter is arranged above the conveying drag chain in the flocking box, the filter being provided with a movable sweeping plate at an upper side of the filter;
the sweeping plate is connected to a second motor by a belt; and
sliders are fixedly arranged on an outer surface of the sweeping plate, slide rails are correspondingly arranged on an inner surface of the flocking box, and the sliders are slidingly arranged on the slide rails.

6. The swab flocking device according to claim 1, wherein:
a plurality of hanging plates are arranged on each swab hanger at a uniform interval, two ends of each hanging plate being fixed to a bottom surface of each swab hanger by fixing grooves respectively;
a plurality of swab sticks are hung on each hanging plate; and
grids are arranged on a circumferential surface of the flocking box in correspondence to the blowers.

7. A flock blowing and flocking process for a swab, which performs flocking using the swab flocking device according to claim 1, comprising the following steps:
hanging a respective swab stick on a respective swab hanger, and conveying the respective swab hanger into the flocking box by the conveying drag chain; and
blowing flocks by the blowers to the end head of the respective swab stick in the flocking box.

8. The flock blowing and flocking process for the swab according to claim 7, wherein the process comprises performing plasma treatment, gluing, and spin coating treatment on the end head of the respective swab stick in sequence, prior to conveying the respective swab stick into the flocking box; and
drying the respective swab stick, after the flock blowing to the respective swab stick is completed.

9. The flock blowing and flocking process for a swab according to claim 7, wherein a flock density of flocking is in a range between 3.8 to 6.0 Dtex, and a flock length is in a range between 0.4 to 0.6 mm.

10. A flock blowing and flocking process for a swab, which performs flocking using the swab flocking device according to claim 2, comprising the following steps:
hanging a respective swab stick on a respective swab hanger, and conveying the respective swab hanger into the flocking box by the conveying drag chain; and
blowing flocks by the blowers to the end head of the respective swab stick in the flocking box.

11. A flock blowing and flocking process for a swab, which performs flocking using the swab flocking device according to claim 3, comprising the following steps:
hanging a respective swab stick on a respective swab hanger, and conveying the respective swab hanger into the flocking box by the conveying drag chain; and
blowing flocks by the blowers to the end head of the respective swab stick in the flocking box.

12. A flock blowing and flocking process for a swab, which performs flocking using the swab flocking device according to claim 4, comprising the following steps:
hanging a respective swab stick on a respective swab hanger, and conveying the respective swab hanger into the flocking box by the conveying drag chain; and
blowing flocks by the blowers to the end head of the respective swab stick in the flocking box.

13. A flock blowing and flocking process for a swab, which performs flocking using the swab flocking device according to claim 5, comprising the following steps:
hanging a respective swab stick on a respective swab hanger, and conveying the respective swab hanger into the flocking box by the conveying drag chain; and
blowing flocks by the blowers to the end head of the respective swab stick in the flocking box.

14. A flock blowing and flocking process for a swab, which performs flocking using the swab flocking device according to claim 6, comprising the following steps:
hanging a respective swab stick on a respective swab hanger, and conveying the respective swab hanger into the flocking box by the conveying drag chain; and
blowing flocks by the blowers to the end head of the respective swab stick in the flocking box.

* * * * *